United States Patent
Resnati et al.

(10) Patent No.: US 9,848,599 B2
(45) Date of Patent: Dec. 26, 2017

(54) CO-CRYSTALS OF 3-IODOPROPYNYL BUTYLCARBAMATE

(71) Applicant: POLITECNICO DI MILANO, Milan (IT)

(72) Inventors: Giuseppe Resnati, Milan (IT); Pierangelo Metrangolo, Milan (IT); Giancarlo Terraneo, Milan (IT); Michele Baldrighi, Milan (IT)

(73) Assignee: POLITECNICO DI MILANO, Milan (IT)

( * ) Notice: Subject to any disclaimer, the term of this patent is extended or adjusted under 35 U.S.C. 154(b) by 202 days.

(21) Appl. No.: 14/391,504

(22) PCT Filed: Apr. 9, 2013

(86) PCT No.: PCT/EP2013/057384
§ 371 (c)(1),
(2) Date: Oct. 9, 2014

(87) PCT Pub. No.: WO2013/153059
PCT Pub. Date: Oct. 17, 2013

(65) Prior Publication Data
US 2015/0051280 A1  Feb. 19, 2015

(30) Foreign Application Priority Data
Apr. 11, 2012  (IT) .............................. MI2012A0586

(51) Int. Cl.
| | | |
|---|---|---|
| A01N 47/10 | (2006.01) | |
| A61K 31/27 | (2006.01) | |
| A01N 25/08 | (2006.01) | |
| A01N 47/12 | (2006.01) | |
| A01N 37/18 | (2006.01) | |

(52) U.S. Cl.
CPC ............. *A01N 25/08* (2013.01); *A01N 37/18* (2013.01); *A01N 47/12* (2013.01)

(58) Field of Classification Search
None
See application file for complete search history.

(56) References Cited

U.S. PATENT DOCUMENTS

2005/0033083 A1* 2/2005 Schneider ............. C07C 269/06
560/157
2006/0229381 A1  10/2006 Bartko

OTHER PUBLICATIONS

Morissette (Advanced Drug Delivery Reviews, 56, 275-300, 2004).*
Aakeroy et al., "Cocrystals: Synthesis, Structure, and Applications" Supramolecular Chemistry: From Molecules to Nanomaterials, Mar. 15, 2012.
Metrangolo et al., "Anion Coordination and Anion-Templated Assembly under Halogen Bonding Control", Crystengcomm, vol. 11, No. 7, Jan. 1, 2009.
Weiss et al., "Stable 1: 1 Adducts from Iodoacetylenes and Iodide Ions: Ion Pair Strain as an Additional Driving Force?" Angw. Chem. Int. Ed. Engl., vol. 34, No. 4, Dec. 31, 1995.
International Search Report and Written Opinion of counterpart International Application No. PCT/EP2013/057384, dated Jul. 15, 2013.

* cited by examiner

*Primary Examiner* — Dennis Heyer
*Assistant Examiner* — Daniel M Podgorski
(74) *Attorney, Agent, or Firm* — Silvia Salvadori, P.C.; Silvia Salvadori

(57) ABSTRACT

The present invention relates to biocidal agents designed to protect industrial products against microbial, bacterial, fungal and algal infections. In particular, the present invention relates to co-crystals containing 3-iodopropynyl butylcarbamate (IPBC) and to compositions containing said co-crystals which possess improved physical, chemical and workability properties compared with the use of IPBC.

7 Claims, 20 Drawing Sheets

CO-CRYSTALS OF 3-IODOPROPYNYL BUTYLCARBAMATE

This application is a U.S. national stage of PCT/EP2013/057384 filed on Apr. 9, 2013, which claims priority to and the benefit of Italian Application No. MI2012A000586 filed on Apr. 11, 2012, the contents of which are incorporated herein by reference in their entireties.

FIELD OF INVENTION

The present invention relates to biocidal agents designed to protect industrial products against microbial, bacterial, fungal and algal infections. In particular, the present invention relates to co-crystals containing 3-iodopropynyl butylcarbamate (IPBC) and to compositions containing said co-crystals which have improved physical, chemical and workability properties compared with the use of IPBC.

DESCRIPTION OF THE STATE OF THE ART

3-Iodopropynyl butylcarbamate (IPBC) is a biocide used as a preservative, fungicide and algaecide in industrial formulations such as paints and coatings, in metalworking and in the protection and preservation of wood. It is also added to polymer formulations to prevent the growth of fungi and bacteria in products obtained from polymers. It is also present in personal care products and cosmetics to prevent the growth of bacteria and fungi.

In some of its applications, IPBC can be added directly to the formulation concerned at room temperature. However, the compound is difficult to use in industrial products and processes. Its solubility in water is extremely low (156 ppm at 20° C.), and it tends to be uneven and sticky, which makes it unsuitable for automatic manufacturing devices. The product melts at the temperature of 67° C., above which it degrades rapidly. It is therefore considered unusable in compositions which must be used above said temperature.

The product can be prepared with high yields and purity as disclosed in U.S. Pat. No. 6,999,208.

The crystalline and molecular structure of IPBC was described by E. V. Avtomonov et al, Zeitschrift fuer Naturforschung, B: Chemical Sciences, 52(2), 256-258, 1997.

Co-crystals between IPBC and a second component are not known.

The definition of co-crystal has long been debated in the crystallography sphere. The simplest definition is a crystalline structure consisting of two or more components in a precise stoichiometric ratio, where each component can be an atom, an ion or a molecule (G. P. Stahly et al., A survey of co-crystals reported prior to 2000, *Crystal Growth & Design*, 9(10), 4212-4229, 2009). However, this definition includes many types of compounds, such as hydrates, solvates and clathrates, so the definition is sometimes extended by specifying that the components of the co-crystals are solid in their pure forms under room conditions (J. H. ter Horst et al, Discovering new co-crystals, *Crystal Growth & Design*. 9 (3), 1531-1537, 2009). Another definition present in the literature is that co-crystals consist of two or more components that form a single crystalline structure having unique properties (G. P. Stahly, Diversity in Single- and Multiple-Component Crystals. The Search for and Prevalence of Polymorphs and Cocrystals, *Crystal Growth & Design* 7(6), 1007-1026, 2007).

Co-crystals are orderly structures, and their components interact through non-covalent interactions, such as hydrogen bonds, ionic interactions, van der Waals interactions and $\pi$ interactions. The properties of co-crystals, such as their melting point, solubility, chemical stability and mechanical properties, differ from those of their individual components.

The formation of co-crystals wherein one of the components is a substance with biological activity is an increasingly common approach in the pharmaceutical industry, because it allows the chemico-physical properties of the active ingredient of interest to be optimised. See, for example: M. J. Zaworokto et al, The role of cocrystals in pharmaceutical science, *Drug Discovery Today*, 13, 440, 2008; O. Almarsson et al, Crystal engineering of the composition of pharmaceutical phases. Do pharmaceutical cocrystals represent a new path to improved medicines? *Chem. Comm.*, 1889, 2004; P. Vishweshwar et al, Pharmaceutical cocrystals. *J. Pharm. Sciences*, 95, 499, 2006; A. V. Trask, An overview of pharmaceutical cocrystals as intellectual property. *Mol. Pharma.* 4, 30, 2007; W. Jones et al., Pharmaceutical cocrystals: an emerging approach to physical property enhancement. *MRS Bull.* 31, 875, 2006.

Examples of co-crystallisation approaches used to generate new supramolecular materials are reported in US2011152266 (A1), GB2476202 (A), CA2738866 (A1), WO2011035456 (A1), KR20100091127 (A), WO2010011926 (A2), WO2010128977 (A1), MX2008015937 (A), KR20090015912 (A), WO2009116055 (A1), US2009247749 (A1), WO2008108639 (A1), US2008280858 (A1), WO2008021559 (A2), WO2007067727 (A2), US2006149521 (A1), CN1757780 (A) and WO2005089375 (A2). In all cases, the co-crystals are formed by non-covalent interactions involving hydrogen bonds, $\pi$-$\pi$ (stacking) interactions or ion-$\pi$ interactions.

Methods for generating new molecular entities involving IPBC are described in US20040143011A1 and U.S. Pat. No. 7,851,516B2. However, these documents do not suggest the formation of co-crystals involving the iodoacetylenyl group and halogen bond interaction like those forming the object of the present application.

Definitions

For the purpose of the present application, "co-crystal" is defined as a crystal that contains in the crystal unit cell at least one molecule of IPBC and at least one molecule of a second compound, called the "co-crystallisation agent", which can be liquid or solid at room temperature.

For the purpose of the present application, the term "halogen bond" (XB) indicates a non-covalent interaction involving the iodine atom of IPBC, which acts as electron density acceptor. This type of bond is indicated in the present application by the graphical representation D - - - I, wherein I is the iodine atom (Lewis acid, electron acceptor, XB-donor) and D is an electron-donor species (Lewis base, XB-acceptor). For a discussion of the halogen bond, see P. Metrangolo, F. Meyer, T. Pilati, G. Resnati, G. Terraneo, Halogen Bonding in Supramolecular Chemistry, *Angewandte Chemie International Edition*, Volume 47(33), 6114-6127, 2008.

DISCLOSURE OF THE INVENTION

The object of the present invention is co-crystals of the compound 3-iodopropynyl butylcarbamate with a co-crystallisation agent, wherein said agent is in the liquid or solid state at room temperature and is bonded to IPBC via at least one halogen bond. The co-crystals according to the invention have more advantageous chemico-physical properties than IPBC, such as better water solubility, greater heat stability, better powder flowability and better compressibility for tablet formation.

The co-crystals according to the invention are obtained by synthesis in the solid state or in solution. They can be formed by a supramolecular approach involving assembly of IPBC with selected chemical species called co-crystallisation agents, which are able to establish non-covalent interactions involving the iodine atom (halogen bond, XB) present on the molecular structure of IPBC. The co-crystallisation agents used in the present invention are: organic bases, in particular aliphatic amines or aromatic heterocyclic derivatives containing at least one basic nitrogen atom; halides; phosphates; and carboxylates.

A further object of the invention is a composition containing a co-crystal as defined above, and additives.

A further object of the invention is the use of a co-crystal as defined above, or a composition as defined above, as a biocide, in particular as a preservative, antibacterial, fungicide or algaecide.

A further object of the invention is industrial products containing a co-crystal as defined above.

Finally, a further object of the invention is a process for the preparation of a co-crystal as defined above, comprising: a) placing IPBC in contact with a co-crystallisation agent able to form at least one halogen bond with said IPBC, under crystallisation conditions such as to form a solid phase wherein the IPBC and said agent are bonded together via at least one halogen bond; and b) optional isolation of the co-crystals formed in step a).

DETAILED DESCRIPTION OF THE INVENTION

In one embodiment of the invention the co-crystallisation agent is selected from aromatic heterocycles containing at least one basic nitrogen atom, and is preferably selected from pyridine, pyrimidine, pyrazine, pyridazine, pyrazole, thiazole, isothiazole, oxazole, isoxazole; their derivatives functionalized with $C_1$-$C_6$ alkyl; $C_2$-$C_6$ alkenyl; $C_2$-$C_6$ alkyl groups containing an epoxy group; $C_3$-$C_7$ cycloalkyl groups; benzyl groups; $C_6$-$C_{10}$ aryl groups; $C_1$-$C_6$ alkoxyl groups; halides; carboxyamide; carbonyl optionally in the form of an acetal or a ketal deriving from a $C_1$-$C_6$ alcohol or optionally in the form of a cyclic ketal deriving from a $C_2$-$C_6$ alkane-1,2-diol or a $C_2$-$C_6$ alkane-1,3-diol; hydroxyl; $C_1$-$C_6$-alkoxycarbonyl groups; sulfhydryl; $C_1$-$C_6$ alkylthio groups; $C_1$-$C_6$-alkylsulfinyl groups; $C_1$-$C_6$-alkylsulfonyl groups; sulfonamide; and benzocondensed derivatives thereof, such as quinoline and isoquinoline.

In one embodiment said aromatic heterocycles useful as co-crystallisation agents are selected from pyridine and derivatives of pyridine of general formula (I)

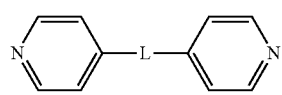

(I)

wherein L is selected from —$(CH_2)_n$—, wherein n is 0 or an integer between 1 and 6, and —C(O)—NH—$(CH_2)_m$—NH—C(O)—, wherein m is an integer between 2 and 6, and wherein in said compound (I) one or both pyridine rings can be benzocondensed.

In a preferred embodiment the compounds of formula (I) are selected from 4,4'-bipyridyl, 4-[2-(4-pyridinyl)ethyl]pyridine and N,N'-bis(4-pyridylcarbonyl)-1,6-hexanediamine.

In another embodiment of the invention the co-crystallisation agent is an aliphatic amine of formula $R^1R^2R^3N$ wherein $R^1$, $R^2$ and $R^3$ are independently selected from the group containing hydrogen, $C_1$-$C_6$ alkyl and $C_3$-$C_7$ cycloalkyl; or $R^1$ is as defined above and $R^2$ and $R^3$, taken together with the nitrogen atom to which they are bonded, form a 4-7 member nitrogenous heterocyclic ring optionally containing one oxygen or sulphur atom or a further nitrogen atom, said further nitrogen atom being substituted by an $R^1$ group as defined above; or the aliphatic amines are selected from the group of bicyclic tertiary amines of formula (II)

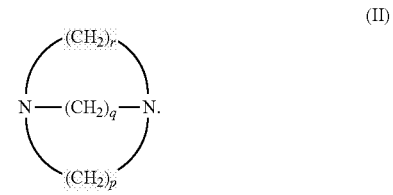

(II)

wherein p, q and r are independently selected from the integers 2 or 3.

Examples of aliphatic amines useful for the purposes of the present invention are triethylamine, diisopropylethylamine, tributylamine, N-methylpiperidine, N-methylmorpholine and N,N'-dimethylpiperazine. In a preferred embodiment the bicyclic tertiary amine of formula (II) is 1,4-diazabicyclo[2.2.2]octane.

In another embodiment of the invention, the co-crystallisation agent is an organic or inorganic halide.

When an organic halide is used, it is preferably a tetraalkyl ammonium halide of formula $R_4N^+X^-$ wherein each R can independently be a $C_1$-$C_6$ alkyl and $X^-$ is a halide.

In a preferred embodiment the organic halide is tetrabutyl ammonium halide, preferably tetrabutyl ammonium chloride or tetrabutyl ammonium iodide.

In another embodiment of the invention, the co-crystallisation agent is an inorganic halide, and is preferably an alkali or alkaline-earth metal or transition metal halide selected from iron and zinc, or a tin halide. Examples of inorganic halides usable as co-crystallisation agents according to the present invention are iodides such as cuprous iodide and potassium iodide; chlorides such as ammonium chloride, magnesium chloride, potassium chloride, stannous chloride, calcium chloride, ferric chloride, sodium chloride and zinc (II) chloride.

In a preferred embodiment the inorganic halide is calcium chloride or zinc (II) chloride.

In another embodiment of the invention, the co-crystallisation agent is an inorganic phosphate, such as monobasic ammonium phosphate, dibasic ammonium phosphate, dibasic magnesium phosphate, tribasic magnesium phosphate, monobasic calcium phosphate, dibasic calcium phosphate, tribasic calcium phosphate, calcium pyrophosphate, ferric phosphate, ferric pyrophosphate, monobasic potassium phosphate, dibasic potassium phosphate, tribasic potassium phosphate, potassium pyrophosphate, sodium aluminium phosphate, monobasic sodium phosphate, dibasic sodium phosphate, tribasic sodium phosphate or sodium pyrophosphate.

In another embodiment of the invention the co-crystallisation agent is an alkali or alkaline-earth metal or transition metal carboxylate. Examples of carboxylates useful for the purpose of the present invention are acetates, such as calcium acetate, sodium acetate and zinc acetate; citrates, such as ammonium citrate, calcium citrate, iron (III) citrate, ammonium iron (III) citrate, sodium citrate and potassium citrate; and benzoates, such as sodium benzoate.

In the co-crystals according to the invention, IPBC and the co-crystallisation agent are present in a molar ratio ranging between 2:1 and 4:1.

The preferred co-crystals according to the invention are:
co-crystal containing 3-iodopropynyl butylcarbamate and pyridine in a 1:1 molar ratio;
co-crystal containing 3-iodopropynyl butylcarbamate and 4-[2-(4-pyridinyl)ethyl]pyridine in a 2:1 molar ratio;
co-crystal containing 3-iodopropynyl butylcarbamate and 4,4'-bipyridine in a 2:1 molar ratio;
co-crystal containing 3-iodopropynyl butylcarbamate and 1,4-diazabicyclo[2.2.2]octane in a 2:1 molar ratio;
co-crystal containing 3-iodopropynyl butylcarbamate and tetrabutyl ammonium iodide in a 3:1 molar ratio;
co-crystal containing 3-iodopropynyl butyl carbamate and tetrabutyl ammonium chloride in a 2:1 molar ratio;
co-crystal containing 3-iodopropynyl butylcarbamate and calcium chloride in a 4:1 molar ratio;
co-crystal containing 3-iodopropynyl butylcarbamate and zinc chloride in a 4:1 molar ratio
co-crystal containing 3-iodopropynyl butylcarbamate and N,N'-bis(4-pyridylcarbonyl)-1,6-hexanediamine in a 2:1 molar ratio.

Further preferred co-crystals according to the invention are:
co-crystal containing 3-iodopropynyl butylcarbamate and 4-[2-(4-pyridinyl)ethyl]pyridine in a 2:1 molar ratio, having characteristic X-ray powder diffraction (XRPD) peaks at 2θ angle values of 5.12, 5.68, 11.44, 16.95, 22.22, 22.66, 24.97 and 27.88±0.05°, and unit cell dimensions [a=30.666(3) b=4.9869(4) c=21.068(2)] and [α=90.00 β=92.115(6) γ=90.00];
co-crystal containing 3-iodopropynyl butylcarbamate and 4,4'-bipyridine in a 2:1 molar ratio, having characteristic X-ray powder diffraction (XRPD) peaks at 2θ angle values of 6.23 and 21.93±0.05°, and unit cell dimensions a=28.683(2) b=4.9270(4) c=21.429(2)] and [α=90.00 β=99.92(2) γ=90.00];
co-crystal containing 3-iodopropynyl butylcarbamate and tetrabutyl ammonium iodide in a 3:1 molar ratio, having characteristic X-ray powder diffraction (XRPD) peaks at 2θ angle values of 9.28, 14.48, 16.32, 17.73, 20.25, 20.69, 21.10, 21.33, 22.26, 22.90, 23.60, 23.97, 24.30, 25.01, 26.13, 26.51, 27.90 and 28.40±0.1°, and unit cell dimensions [a=10.7688(9) b=20.204(2) c=23.735(2)] and [α=90.00 β=94.778(2) γ=90.00];
co-crystal containing 3-iodopropynyl butylcarbamate and calcium chloride in a 4:1 molar ratio, having characteristic X-ray powder diffraction peaks (XRPD) at 2θ angle values of 9.67 and 22.28±0.05°;
co-crystal containing 3-iodopropynyl butylcarbamate and N,N'-bis(4-pyridylcarbonyl)-1,6-hexanediamine in a 2:1 molar ratio, having characteristic X-ray powder diffraction (XRPD) peaks at 2θ angle values of 11.83 and 22.78±0.05°, and unit cell dimensions [a=29.4501(18) b=5.1100(3) c=27.9417(17)] and [α=90.00 β=118.566(3) γ=90.00];
co-crystal containing 3-iodopropynyl butylcarbamate and pyridine in a 1:1 molar ratio, having a $^{13}$C-NMR spectrum substantially as depicted in FIG. 20 wherein the chemical shift may vary from 4.00 ppm up to 14 ppm;
co-crystal containing 3-iodopropynyl butylcarbamate and 1,4-diazabicyclo[2.2.2]octane (DABCO) in a 2:1 molar ratio, having an orthorhombic unit cell, Pccn, a: 9.8955(7); b: 31.623(2); c: 8.9335(6) and V=2795.55 $A^3$;
co-crystal containing 3-iodopropynyl butylcarbamate and tetrabutylammonium chloride in a 2:1 molar ratio, having an IR spectrum substantially as depicted in FIG. 22;
co-crystal containing 3-iodopropynyl butylcarbamate and zinc chloride in a 4:1 molar ratio, having a DSC plot substantially as depicted in FIG. 23, showing two peaks at 118° C. and 139° C.

"Characteristic peaks in the XRPD spectrum" means peaks with a relative intensity exceeding 40% compared with the peak of greatest intensity, taken as 100.

The crystallisation methods used to prepare the co-crystals according to the invention comprise slow and fast evaporation of solutions containing IPBC and the co-crystallisation agent in the desired stoichiometric ratios, wherein the formation of the co-crystal takes place in solution by slow and fast evaporation of the solvent; fast precipitation from quasi-saturated solvent solutions containing IPBC and the co-crystallisation agent; grinding (dry or in the presence of drops of solvent) of a mixture of IPBC and the co-crystallisation agent; melting of the mixture of IPBC and the co-crystallisation agent; mechano-chemical solid-phase synthesis in a ball mill; or a combination of said methods. The choice of one or more of said methods is made on the basis of the physical state (solid or liquid) of the IPBC and/or the co-crystallisation agent at the temperature at which the formation of the co-crystal is conducted.

In one embodiment of the invention, the co-crystals are synthesised in solution.

If both IPBC and the co-crystallisation agent are in the solid state, each substance, in the exact molar ratios, is dissolved separately in a suitable solvent, such as methanol, ethanol, chloroform, dichloromethane, acetonitrile or ethyl acetate. The two solutions are then mixed together, and the resulting mixture is left to evaporate. The evaporation is performed slowly if a single crystal is to be obtained or rapidly, for example with the aid of a vacuum evaporation system, if the co-crystal is to be obtained in powder form.

However, if the co-crystallisation agent is a liquid, a quasi-saturated solution of IPBC is prepared in a suitable solvent, such as methanol, ethanol, chloroform, dichloromethane, acetonitrile or ethyl acetate. The liquid co-crystallisation agent is then added to said solution in an exact molar ratio. The resulting mixture is left to evaporate. The evaporation is performed slowly if a single crystal is to be obtained or rapidly, for example with the aid of a vacuum evaporation system, if the co-crystal is to be obtained in powder form.

In another embodiment of the invention, the co-crystals are synthesised in the solid state. IPBC and the co-crystallisation agent, weighed in the exact molar ratio desired for the co-crystal, are mixed together and placed in a metal container of various dimensions. One or more metal balls of various dimensions are introduced into the container. The container is placed in a ball mill and vibrated with a frequency of 10-30 Hz for a time ranging between 5 and 30 minutes, depending on the dimensions of the container. The product recovered from the container is the co-crystal, which requires no further purification.

The co-crystals according to the invention containing IPBC are suitable to protect industrial materials such as adhesives, glues, paper, cardboard, leather, wood and wood-based materials, coating materials, paints, plastic materials, industrial coolants, industrial lubricants, metalworking fluids, body care products such as wet wipes, toilet paper, cosmetics, and other materials which can be infested or decomposed by micro-organisms. Examples of micro-organisms which can cause the degradation or deterioration of industrial materials, against which the co-crystals according to the invention can be advantageously used, are bacteria, fungi (in particular fungi and moulds that attack wood), yeasts, algae and mucous organisms such as slime. Specific examples are micro-organisms of the genus *Alternaria*, such as *Alternaria tenuis*, *Aspergillus*, such as *Aspergillus niger*, *Chaetomium*, such as *Chaetomium globosum*, *Coniophora*, such as *Coniophora puetana*, *Lentinus*, such as *Lentinus tigrinus*, *Penicillium*, such as *Penicillium glaucum*, *Polyporus*, such as *Polyporus versicolor*, *Aureobasidium*, such as *Aureobasidium pullulans*, *Sclerophoma*, such as *Sclerophoma pityophila*, *Trichoderma*, such as *Trichoderma viride*, *Escherichia*, such as *Escherichia coli*, *Pseudomonas*, such as *Pseudomonas aeruginosa*, and *Staphylococcus*, such as *Staphylococcus aureus*.

Depending on their chemico-physical properties, the co-crystals according to the invention can be incorporated in formulations such as solutions, emulsions, suspensions, powders, foams, pastes, granules, tablets and inhalers, or microencapsulated in polymers. The formulations according to the invention can be prepared by conventional methods. For example, the formulations can be prepared by mixing the co-crystals with diluents, such as liquid solvents or gases liquefied under pressure, and/or with solid diluents, if necessary also using surfactants, such as emulsifying agents and/or dispersing agents and/or foaming agents. If the diluent used is water, organic solvents can also be used as co-solvents. The solvents usable are aromatic solvents such as toluene and xylene; chlorinated aliphatic or aromatic hydrocarbons such as dichloromethane and chlorobenzene; aliphatic hydrocarbons such as cyclohexane; alcohols such as butanol, ethylene glycol and their ethers and esters; ketones such as acetone and ethyl methyl ketone, or cyclohexanone; highly polar solvents such as water, dimethyl sulphoxide and dimethylformamide. Examples of gases liquefied under pressure are liquids which are gaseous at room pressure and temperature, such as halogenated hydrocarbons, butane, propane, nitrogen and carbon dioxide.

Suitable solid diluents are pulverised natural or synthetic minerals such as kaolins, clays, talc, gypsum, quartz, fossil flours, and silica, alumina and silicate powders.

Suitable emulsifying and/or foaming agents are, for example, non-ionic or anionic emulsifying agents such as polyoxyethylene esters with fatty acids, ethers between polyoxyethylene and fatty alcohols, alkyl- or aryl-sulphonates, and alkylsulphates. An example of a suitable dispersing agent is methylcellulose.

The formulations generally contain between 0.1% and 95% by weight of the co-crystals, preferably between 2% and 75% by weight.

A further object of the present invention is therefore compositions with a biocidal activity containing a co-crystal of IPBC according to the invention and at least one solvent or diluent. The compositions according to the invention can also contain additives which assist the process of obtaining the composition and, if necessary, other biocidal agents such as agents with an antimicrobial, fungicidal, bactericidal, herbicidal, insecticidal or algaecidal activity. In this case, the co-crystals according to the invention and the other biocidal agents can be present in solution, suspension or emulsion. The solvents or diluents can be water or conventional organic solvents. Compositions containing a co-crystal according to the invention and another biocidal agent as active ingredients can present a broader action spectrum than the individual active ingredients and/or a synergic effect. Examples of other biocidal agents which can be present in the compositions according to the invention include azaconazole, bromuconazole, cyproconazole, dichlorobutrazole, diniconazole, diuron, hexaconazole, metconazole, penconazole, propiconazole, tebuconazole, dichlofluanid, tolylfluanid, fluorfolpet, methfuroxam, carboxin, cyclohexyl-benzo[b]thiophene carboxamide S,S-dioxide, fenpiclonil, 4-(2,2-difluoro-1,3-benzodioxol-4-yl)-1H-pyrrole-3-carbonitrile, butenafine, imazalil, N-methyl-isothiazolin-3-one, 5-chloro-N-methyl-isothiazolin-3-one, N-octyl-isothiazolin-3-one, dichloro-N-octyl-isothiazolinone, mercaptobenzothiazole, thiocyano-methylthiobenzothiazole, tiabendazole, benzisothiazolinone, N-(2-hydroxypropyl)aminomethanol, benzyl hemiformal, N-methylolchloroacetamide, N-(2-hydroxypropyl)aminomethanol, glutaraldehyde, omadine, Zn-omadine, dimethyl dicarbonate, 2-bromo-2-nitro-1,3-propanediol, bethoxazin, o-phthaldialdehyde, 2,2-dibromo-3-cyano-propionamide, 1,2-dibromo-2,4-dicyano-butane, 1,3-bis(hydroxymethyl)-5,5-dimethylimidazolidine-2,4-dione (DMDMH), tetramethylolacetylenediurea (TMAD), ethylene glycol hemiformal, p-hydroxybenzoic acid and p-hydroxybenzoic acid esters (parabens), such as ethyl p-hydroxybenzoate (E214), ethyl-p-hydroxybenzoate sodium salt (E215), propyl p-hydroxybenzoate (E216), propyl p-hydroxybenzoate sodium salt (E217), methyl-p-hydroxybenzoate (E218) and methyl-p-hydroxybenzoate sodium salt (E219), carbendazim, chlorophene, 3-methyl-4-chlorophenol and o-phenylphenol.

The weight ratio between the co-crystals of the invention and the other biocidal agents can vary within a wide range. Said ratio preferably ranges between 50:1 and 1:50.

The compositions with antimicrobial activity of the invention contain the co-crystals of the invention or a mixture of the co-crystals of the invention and another biocidal agent in a concentration of between 0.1% and 95% by weight, preferably between 0.1% and 60% by weight.

The concentrations at which the co-crystals of the invention or their combination with another biocidal agent are used depend on the nature and incidence of the micro-organisms to be controlled, and the composition of the material to be protected. The ideal quantity for use can be determined by a series of tests. In general, for most applications the concentration is between 0.001% and 5% by weight, preferably between 0.05% and 2% by weight, depending on the material to be protected.

Compositions containing the co-crystals of the invention have better physical and chemical properties (such as greater solubility in water and greater heat stability) and workability properties (such as better powder flowability and better compressibility for tablet formation) than compositions containing IPBC.

A further object of the invention is therefore the use of a co-crystal or composition of the invention as biocide in industrial products, in particular as a preservative, antibacterial, fungicide or algaecide, especially in paints, coatings, metalworking fluids, protection and preservation of wood, and in body care products or cosmetic formulations.

The invention will now be illustrated by the following examples.

EXAMPLES

Materials and Methods

The IR spectra were obtained with a Nicolet Nexus FTIR spectrophotometer equipped with the U-ATR device. The values are reported as wave numbers, and are rounded to 1 cm$^{-1}$ after automatic assignment. The melting points were obtained by differential scanning calorimetry (DSC, Mettler Toledo 823e).

Single-Crystal X-Ray Diffraction

The data were collected at different temperatures with a Bruker KAPPA APEX II diffractometer with Mo-Kα radiation (λ=0.71073) and a CCD detector. The Bruker KRYO-FLEX device was used for the low-temperature acquisitions. The structures were resolved and refined with the SIR2004 and SHELXL-97 programs respectively. The refinement was performed by the full-matrix least squares method on F$^2$. The hydrogen atoms were placed using standard geometric models and with their thermal parameters based on those of their geminal atoms.

X-Ray Powder Diffraction

The X-ray powder diffraction experiments were conducted with a Bruker D8 Advance diffractometer operating in reflection mode with Ge-monochromatic Cu Kα1 radiation (λ=1.5406 Å) and with a position-sensitive linear detector. The powder diffraction data was collected at room temperature with a 2θ interval of 5-40°, using increments of 0.016° and an exposure time of 1.5 s per increment.

Example 1

Co-crystal containing 3-iodopropynyl butylcarbamate and 4-[2-(4-pyridinyl)ethyl]pyridine in a 2:1 Molar Ratio (Co-Crystal 1)

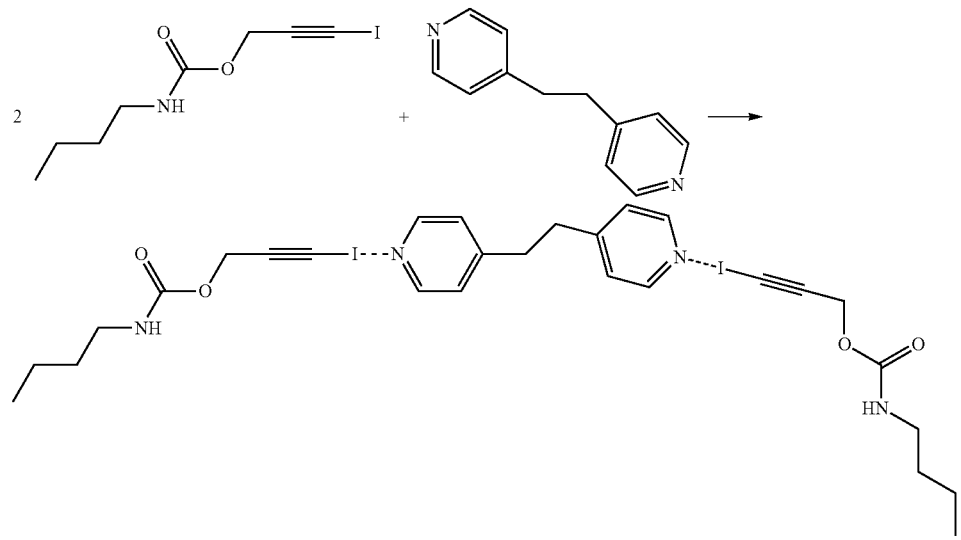

This example demonstrates the ability of IPBC to co-crystallise with a neutral aromatic amine able to act as halogen bond acceptor, such as 4-[2-(4-pyridinyl)ethyl]pyridine.

Rapid precipitation of the two compounds in a quasi-saturated acetonitrile solution leads to the formation of a solid white powder with a melting point of between 81° C. and 83° C.

Figure 1:
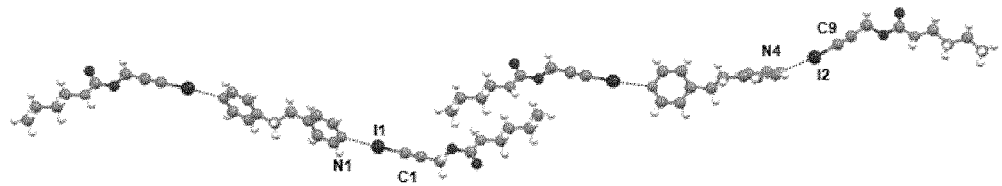
FIG. 1: Graphical representation of the co-crystal of example 1.

Single-crystal X-ray diffraction demonstrates that in the co-crystal, IPBC and 4-[2-(4-pyridinyl)ethyl]pyridine are present in a molar ratio of 2:1, as shown in FIG. 1. The basic structural pattern in the co-crystal is a trimer unit wherein 4-[2-(4-pyridinyl)ethyl]pyridine acts as bridge between two IPBC molecules via two halogen bonds I$^-$$^-$$^-$N.

The dimensions and angles of the crystallographic unit cell are [a=30.666(3) b=4.9869(4) c=21.068(2)] and [α=90.00 β=92.115(6) γ=90.00] respectively.

Figure 2:
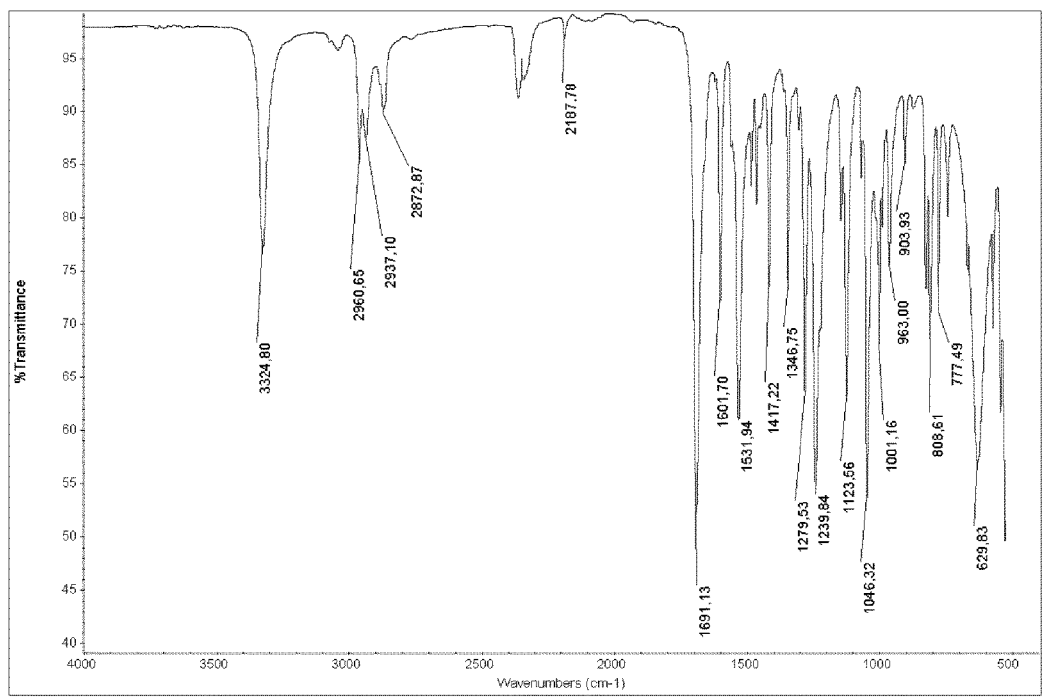
FIG. 2: IR spectrum of the co-crystal of example 1.

The IR spectrum of the co-crystal and its characteristic bands are reported in FIG. 2.

Figure 3:
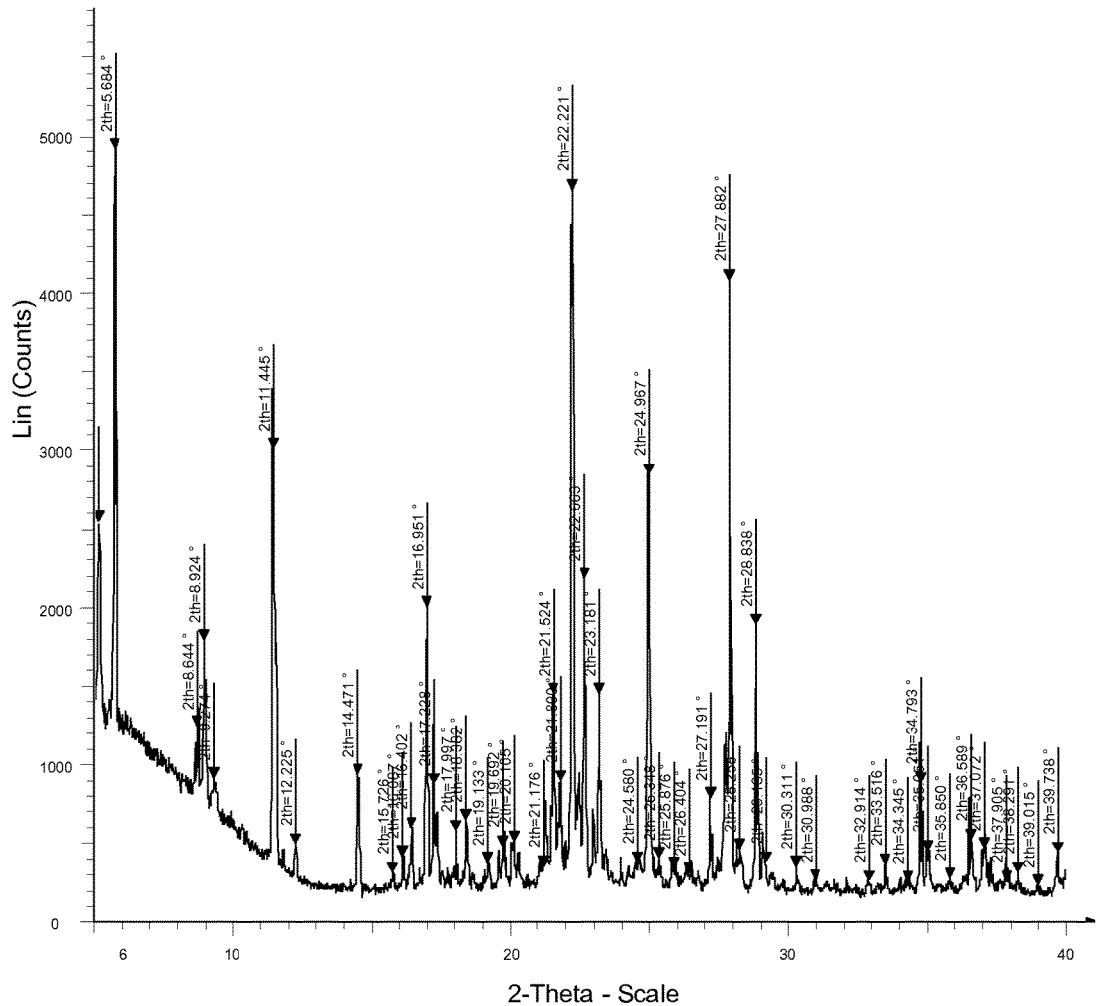
FIG. 3: XRPD tracing of the co-crystal of example 1.

FIG. 3 shows the X-ray powder diffraction (XRPD) of the co-crystal, the main peaks of which, in the 5-40° 2θ value range, are shown in Table 1.

Figure 4:
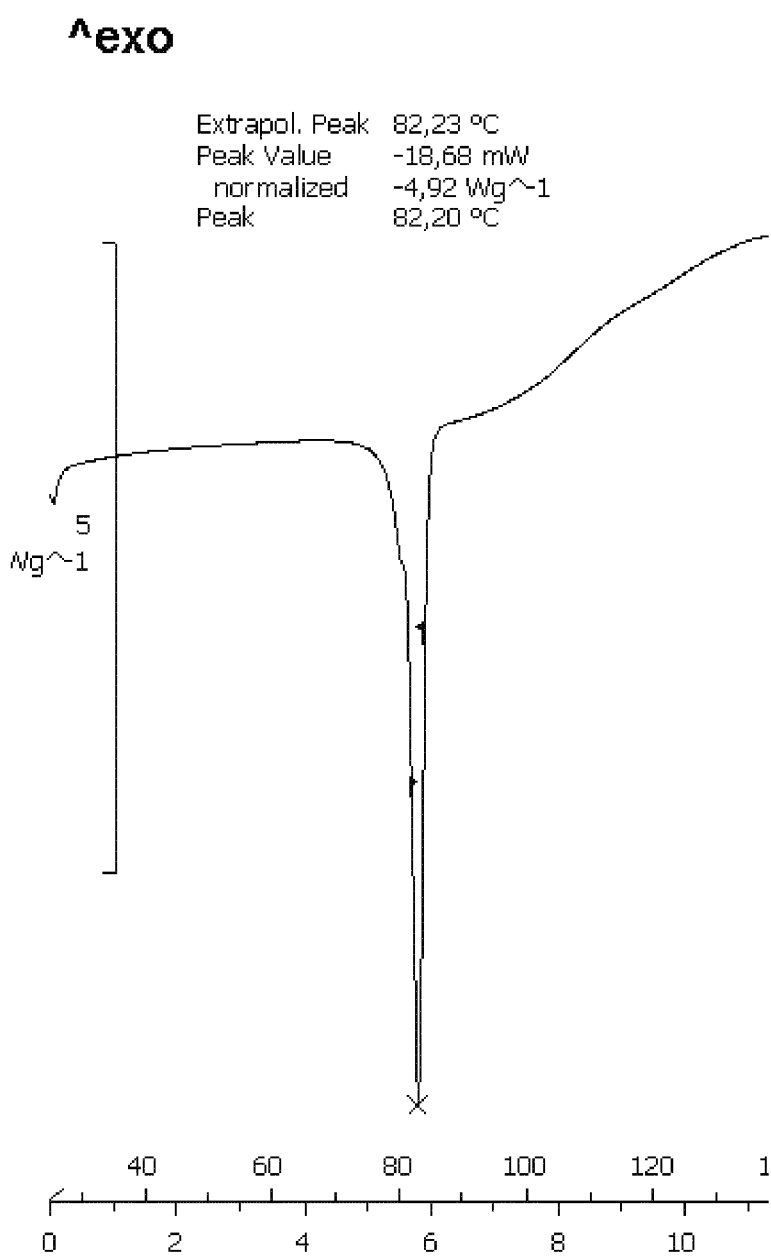
FIG. 4: DSC tracing of the co-crystal of example 1.

The DSC thermogram of co-crystal 1 is reported in FIG. 4.

TABLE 1

| Angle(2θ)* | d (Å) | Intensity | % |
| --- | --- | --- | --- |
| 2th = 5.117° | 17.25577 | 2521 | 51.2 |
| 2th = 5.684° | 15.53601 | 4923 | 100.0 |
| 2th = 8.644° | 10.22081 | 1240 | 25.2 |
| 2th = 8.924° | 9.90129 | 1792 | 36.4 |
| 2th = 9.274° | 9.52842 | 907 | 18.4 |
| 2th = 11.445° | 7.72521 | 3010 | 61.1 |
| 2th = 12.225° | 7.23443 | 490 | 10.0 |

TABLE 1-continued

| Angle(2θ)* | d (Å) | Intensity | % |
| --- | --- | --- | --- |
| 2th = 14.471° | 6.11592 | 932 | 18.9 |
| 2th = 15.726° | 5.63077 | 310 | 6.3 |
| 2th = 16.087° | 5.50517 | 408 | 8.3 |
| 2th = 16.402° | 5.40011 | 592 | 12.0 |
| 2th = 16.951° | 5.22630 | 2000 | 40.6 |
| 2th = 17.228° | 5.14312 | 872 | 17.7 |
| 2th = 17.997° | 4.92493 | 576 | 11.7 |
| 2th = 18.382° | 4.82269 | 644 | 13.1 |
| 2th = 19.133° | 4.63491 | 368 | 7.5 |
| 2th = 19.692° | 4.50459 | 476 | 9.7 |
| 2th = 20.105° | 4.41308 | 507 | 10.3 |
| 2th = 21.176° | 4.19213 | 350 | 7.1 |
| 2th = 21.524° | 4.12518 | 1449 | 29.4 |
| 2th = 21.800° | 4.07364 | 894 | 18.2 |
| 2th = 22.221° | 3.99734 | 4665 | 94.8 |
| 2th = 22.663° | 3.92047 | 2184 | 44.4 |
| 2th = 23.181° | 3.83400 | 1450 | 29.5 |
| 2th = 24.580° | 3.61886 | 373 | 7.6 |
| 2th = 24.967° | 3.56356 | 2850 | 57.9 |
| 2th = 25.348° | 3.51083 | 400 | 8.1 |
| 2th = 25.876° | 3.44043 | 339 | 6.9 |
| 2th = 26.404° | 3.37283 | 302 | 6.1 |
| 2th = 27.191° | 3.27701 | 783 | 15.9 |
| 2th = 27.882° | 3.19725 | 4091 | 83.1 |
| 2th = 28.258° | 3.15564 | 451 | 9.2 |
| 2th = 28.838° | 3.09341 | 1892 | 38.4 |
| 2th = 29.185° | 3.05747 | 373 | 7.6 |
| 2th = 30.311° | 2.94642 | 344 | 7.0 |
| 2th = 30.988° | 2.88354 | 260 | 5.3 |
| 2th = 32.914° | 2.71904 | 255 | 5.2 |
| 2th = 33.516° | 2.67160 | 361 | 7.3 |
| 2th = 34.345° | 2.60901 | 250 | 5.1 |
| 2th = 34.793° | 2.57641 | 883 | 17.9 |

TABLE 1-continued

| Angle(2θ)* | d (Å) | Intensity | % |
| --- | --- | --- | --- |
| 2th = 35.051° | 2.55803 | 443 | 9.0 |
| 2th = 35.850° | 2.50285 | 270 | 5.5 |
| 2th = 36.589° | 2.45396 | 519 | 10.5 |
| 2th = 37.072° | 2.42311 | 464 | 9.4 |
| 2th = 37.905° | 2.37175 | 254 | 5.2 |
| 2th = 38.291° | 2.34872 | 309 | 6.3 |
| 2th = 39.015° | 2.30676 | 228 | 4.6 |
| 2th = 39.738° | 2.26645 | 438 | 8.9 |

*Values ± 0.05°

The co-crystal thus obtained has a higher melting point, higher thermal stability, better workability and higher degree of crystallinity than IPBC. It is easily manageable in the operations required to form tablets, such as compression.

Example 2

Co-Crystal Containing 3-iodopropynyl butylcarbamate and 4,4'-bipyridine in a 2:1 Molar Ratio (Co-Crystal 2)

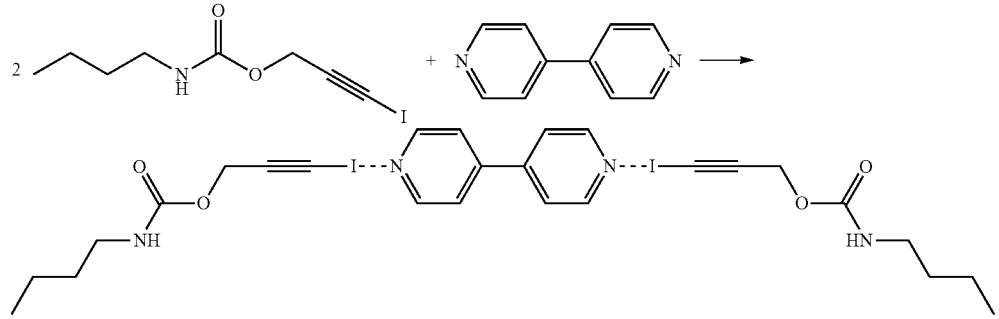

This example demonstrates the ability of IPBC to co-crystallise with another neutral aromatic amine able to act as halogen bond acceptor, such as 4,4'-dipyridine.

In this case the formation of the co-crystal was effected by slow precipitation from an ethanol solution, which leads to the formation of a white powder.

Figure 5:
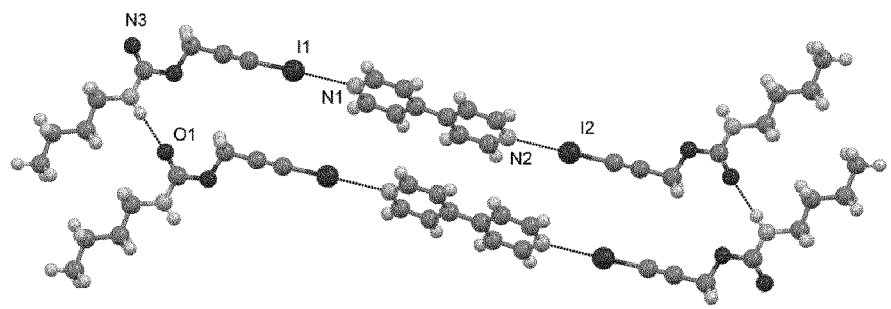
FIG. 5: Graphical representation of the co-crystal of example 2.

The basic structural motif in the co-crystal is a trimeric unit, bonded via halogen bonds, consisting of one molecule of 4,4'-bipyridine and two molecules of IPBC, as shown in FIG. 5.

The co-crystal is a solid crystalline product with a melting point of between 112° C. and 114° C. The dimensions and angles of the crystallographic unit cell are [a=28.683(2) b=4.9270(4) c=21.429(2)] and [α=90.00 β=99.92(2) γ=90.00] respectively.

Figure 6:
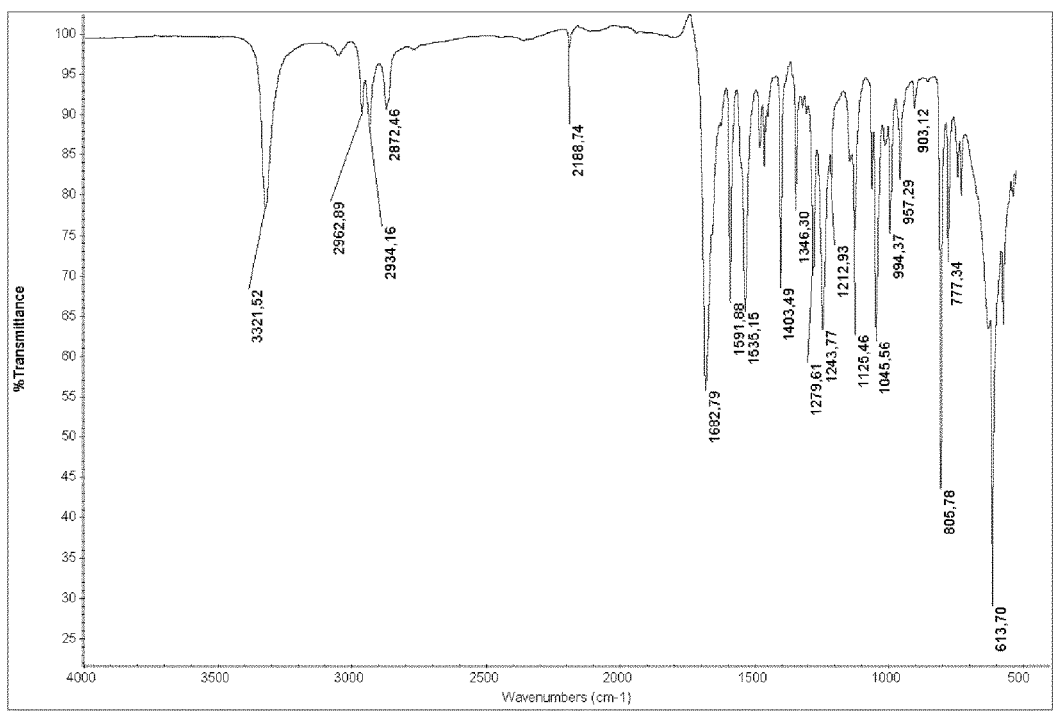
FIG. 6: IR spectrum of the co-crystal of example 2.

The IR spectrum of the co-crystal and its characteristic bands are reported in FIG. 6.

Figure 7:
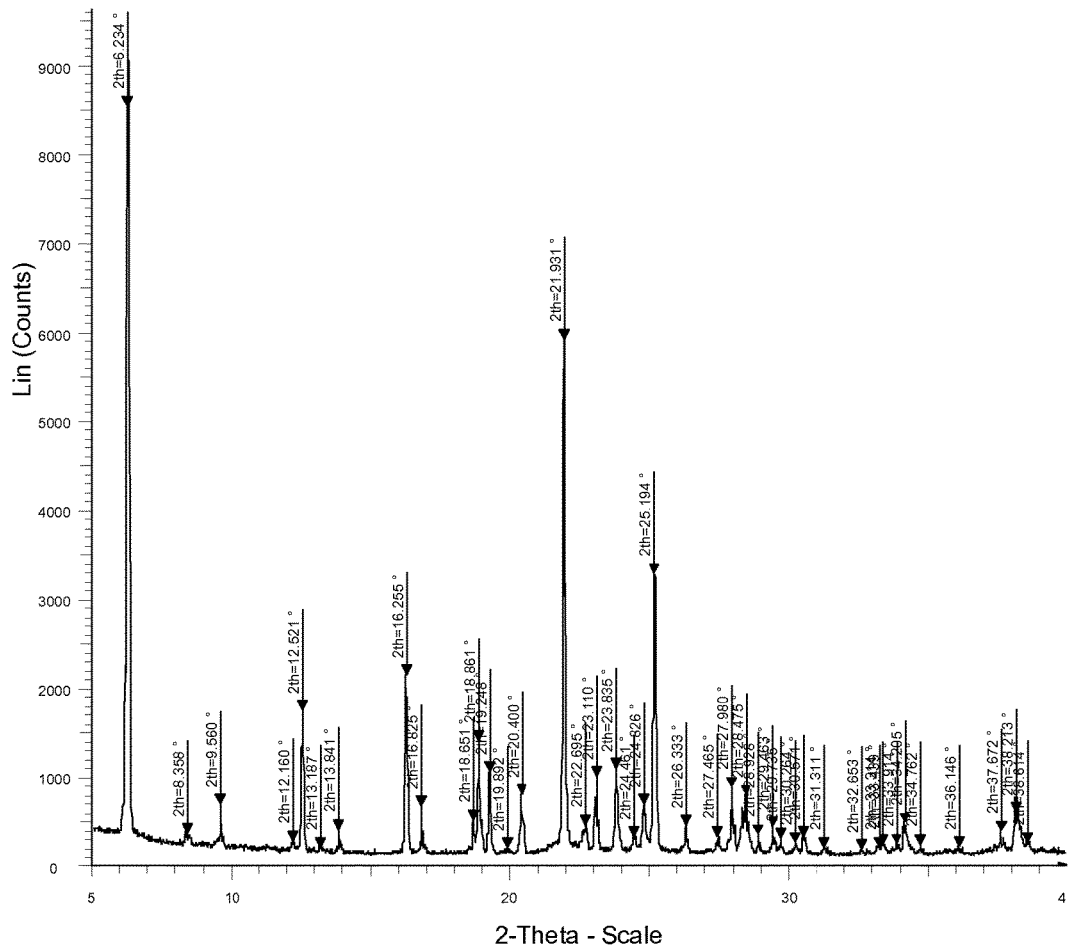
FIG. 7: XRPD tracing of the co-crystal of example 2.

FIG. 7 shows the X-ray powder diffraction (XRPD) of the co-crystal, the main peaks of which, in the 5-40° 2θ value range, are shown in Table 2.

Figure 8:
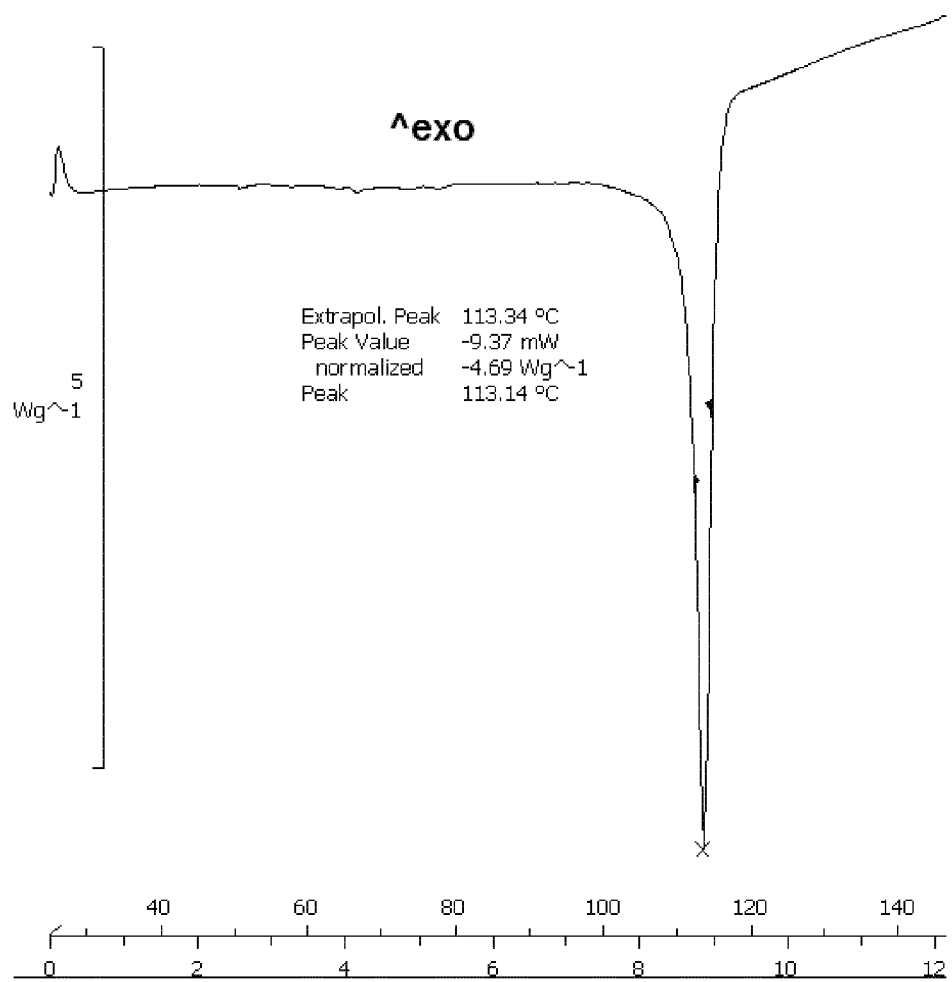
FIG. 8: DSC tracing of the co-crystal of example 2.

The DSC thermogram of co-crystal 2 is reported in FIG. 8.

TABLE 2

| Angle(2θ)* | d (Å) | Intensity | % |
| --- | --- | --- | --- |
| 2th = 6.234° | 14.16728 | 8558 | 100.0 |
| 2th = 8.358° | 10.57069 | 353 | 4.1 |
| 2th = 9.560° | 9.24440 | 679 | 7.9 |
| 2th = 12.160° | 7.27286 | 269 | 3.1 |

TABLE 2-continued

| Angle(2θ)* | d (Å) | Intensity | % |
|---|---|---|---|
| 2th = 12.521° | 7.06371 | 1737 | 20.3 |
| 2th = 13.187° | 6.70850 | 197 | 2.3 |
| 2th = 13.841° | 6.39289 | 399 | 4.7 |
| 2th = 16.255° | 5.44854 | 2148 | 25.1 |
| 2th = 16.825° | 5.26536 | 663 | 7.7 |
| 2th = 18.651° | 4.75371 | 507 | 5.9 |
| 2th = 18.861° | 4.70134 | 1402 | 16.4 |
| 2th = 19.248° | 4.60750 | 1051 | 12.3 |
| 2th = 19.892° | 4.45974 | 187 | 2.2 |
| 2th = 20.400° | 4.34990 | 797 | 9.3 |
| 2th = 21.931° | 4.04952 | 5931 | 69.3 |
| 2th = 22.695° | 3.91488 | 453 | 5.3 |

TABLE 2-continued

| Angle(2θ)* | d (Å) | Intensity | % |
|---|---|---|---|
| 2th = 23.110° | 3.84554 | 991 | 11.6 |
| 2th = 23.835° | 3.73028 | 1084 | 12.7 |
| 2th = 24.461° | 3.63616 | 319 | 3.7 |
| 2th = 24.826° | 3.58348 | 679 | 7.9 |
| 2th = 25.194° | 3.53200 | 3287 | 38.4 |
| 2th = 26.333° | 3.38179 | 452 | 5.3 |
| 2th = 27.465° | 3.24488 | 325 | 3.8 |
| 2th = 27.980° | 3.18637 | 877 | 10.2 |
| 2th = 28.475° | 3.13207 | 786 | 9.2 |
| 2th = 28.928° | 3.08399 | 349 | 4.1 |
| 2th = 29.463° | 3.02919 | 427 | 5.0 |
| 2th = 29.735° | 3.00209 | 298 | 3.5 |
| 2th = 30.264° | 2.95086 | 255 | 3.0 |
| 2th = 30.571° | 2.92189 | 319 | 3.7 |
| 2th = 31.311° | 2.85455 | 198 | 2.3 |
| 2th = 32.653° | 2.74021 | 176 | 2.1 |
| 2th = 33.314° | 2.68732 | 203 | 2.4 |
| 2th = 33.439° | 2.67760 | 232 | 2.7 |
| 2th = 33.914° | 2.64116 | 241 | 2.8 |
| 2th = 34.205° | 2.61934 | 475 | 5.6 |
| 2th = 34.762° | 2.57862 | 234 | 2.7 |
| 2th = 36.146° | 2.48303 | 206 | 2.4 |
| 2th = 37.672° | 2.38589 | 384 | 4.5 |

TABLE 2-continued

| Angle(2θ)* | d (Å) | Intensity | % |
|---|---|---|---|
| 2th = 38.213° | 2.35331 | 596 | 7.0 |
| 2th = 38.614° | 2.32980 | 258 | 3.0 |

*Values ± 0.05°

The co-crystal thus obtained has a higher melting point, higher thermal stability, better workability and higher degree of crystallinity than IPBC. It is easily manageable in the operations required to form tablets, such as compression.

Example 3

Co-Crystal Containing 3-iodopropynyl butylcarbamate and tetrabutyl ammonium iodide in a 3:1 Molar Ratio (Co-Crystal 3)

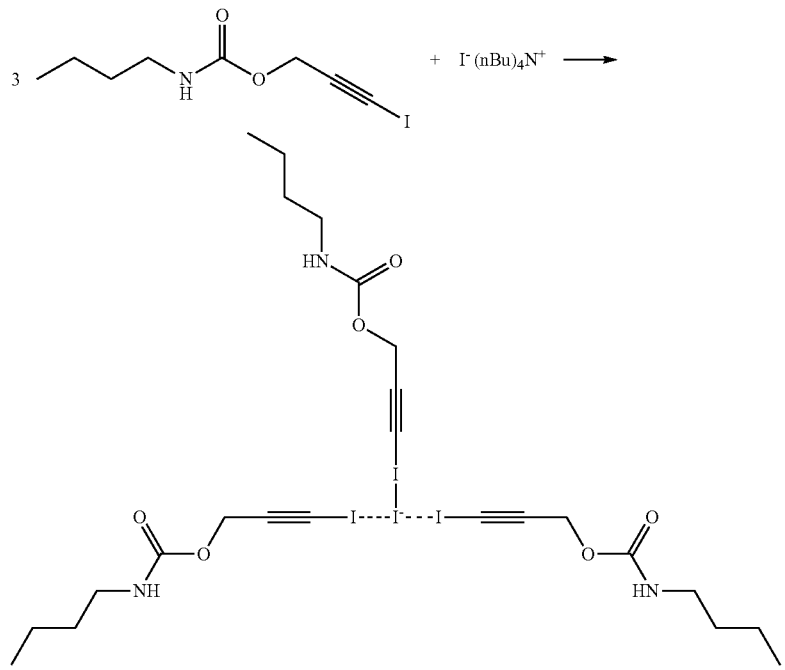

This example demonstrates the ability of IPBC to co-crystallise with a halide deriving from an organic salt such as tetrabutylammonium iodide.

The co-crystal was formed by mechano-chemical synthesis in a ball mill, using a stoichiometric ratio of 1:3 between tetrabutyl ammonium iodide and IPBC.

Figure 9:
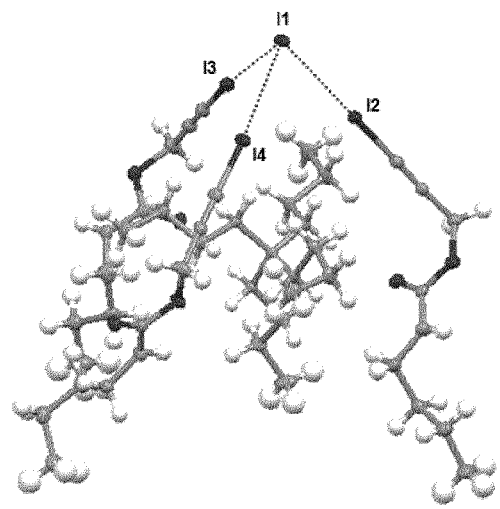
FIG. 9: Graphical representation of the co-crystal of example 3.

The co-crystal obtained contains one molecule of tetrabutyl ammonium iodide and three molecules of IPBC, as shown in the graphical representation in FIG. 9.

The co-crystal is a solid crystalline product with a melting point between 42° C. and 47.5° C. The dimensions and angles of the crystallographic unit cell are a=10.7688(9) b=20.204(2) c=23.735(2)] and [α=90.00 β=94.778(2) γ=90.00] respectively.

Figure 10:
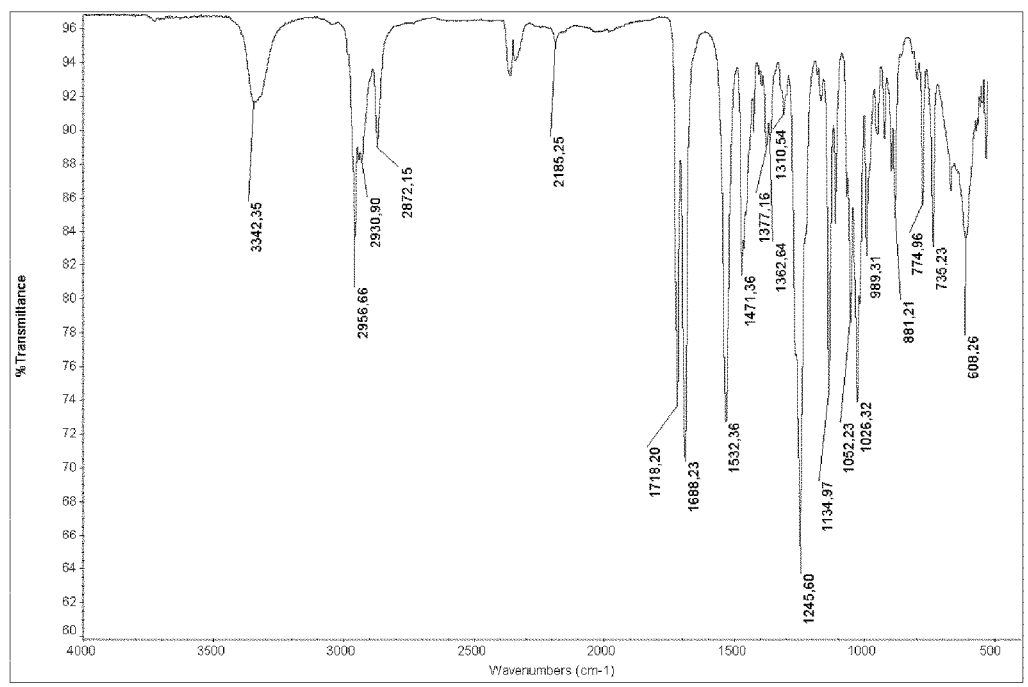
FIG. 10: API IR spectrum of the co-crystal of example 3.

The IR spectrum of the co-crystal and its characteristic bands are reported in FIG. 10.

Figure 11:
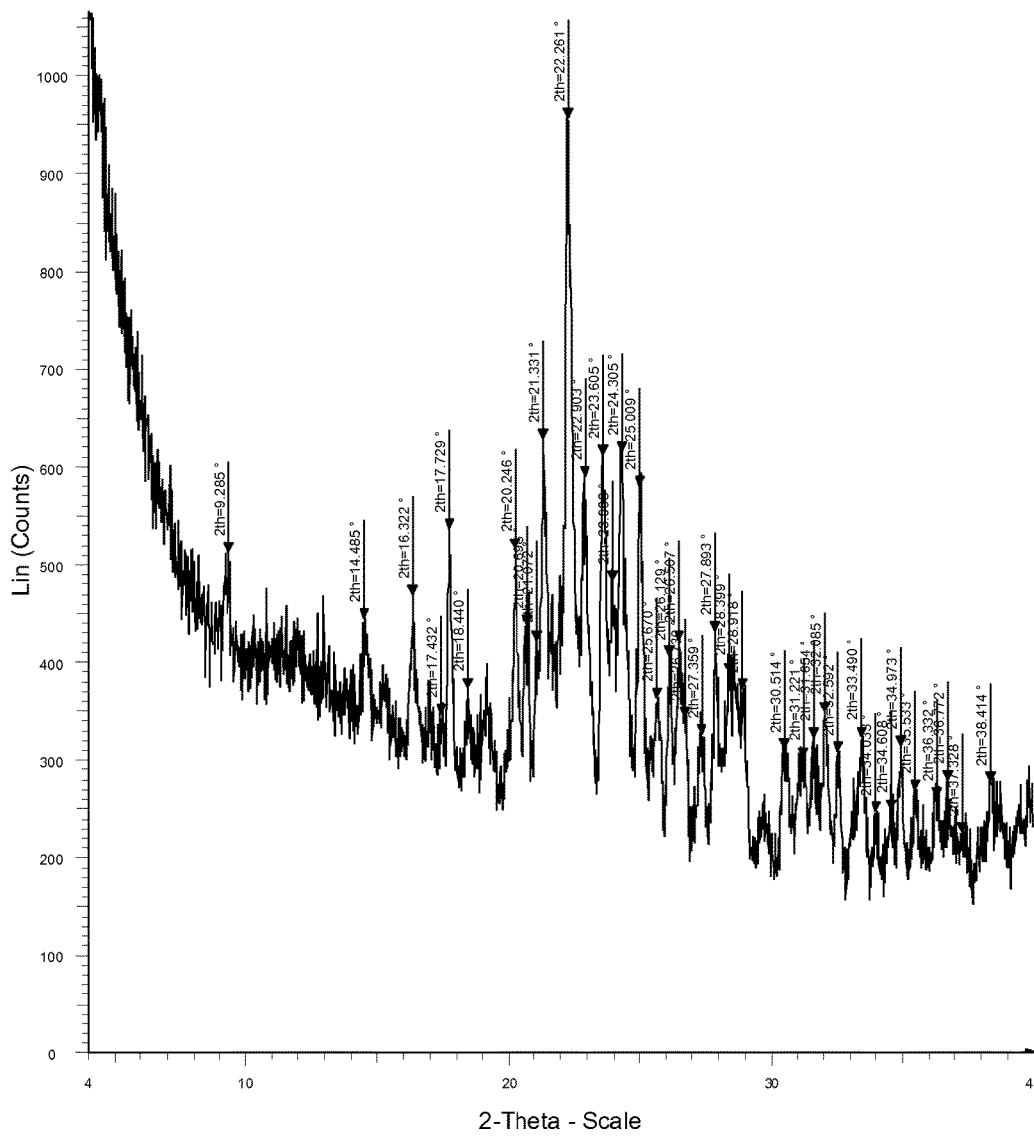
FIG. 11: XRPD tracing of the co-crystal of example 3.

FIG. 11 shows the X-ray powder diffraction (XRPD) of the co-crystal, the main peaks of which, in the 5-40° 2θ value range, are shown in Table 3.

Figure 12:
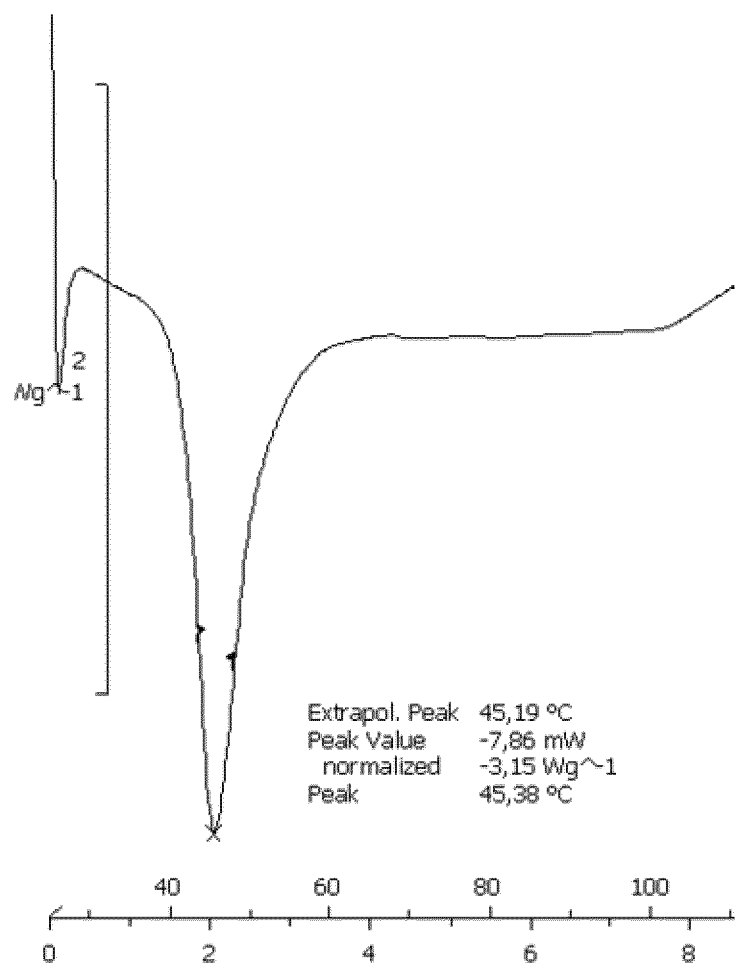
FIG. 12: DSC tracing of the co-crystal of example 3.

The DSC thermogram of co-crystal 3 is reported in FIG. 12.

TABLE 3

| Angle(2θ)* | d (Å) | Intensity | % |
|---|---|---|---|
| 2th = 9.285° | 9.51690 | 513 | 53.5 |
| 2th = 14.485° | 6.11006 | 445 | 46.5 |
| 2th = 16.322° | 5.42635 | 469 | 49.0 |
| 2th = 17.432° | 5.08330 | 346 | 36.1 |
| 2th = 17.729° | 4.99868 | 537 | 56.1 |
| 2th = 18.440° | 4.80755 | 373 | 38.9 |
| 2th = 20.246° | 4.38272 | 517 | 54.0 |
| 2th = 20.698° | 4.28791 | 438 | 45.7 |
| 2th = 21.072° | 4.21276 | 423 | 44.2 |
| 2th = 21.331° | 4.16217 | 629 | 65.7 |
| 2th = 22.261° | 3.99035 | 958 | 100.0 |
| 2th = 22.903° | 3.87977 | 590 | 61.6 |
| 2th = 23.605° | 3.76596 | 613 | 64.0 |
| 2th = 23.968° | 3.70974 | 484 | 50.5 |
| 2th = 24.305° | 3.65910 | 616 | 64.3 |
| 2th = 25.009° | 3.55775 | 580 | 60.5 |
| 2th = 25.670° | 3.46761 | 363 | 37.9 |
| 2th = 26.129° | 3.40770 | 406 | 42.4 |
| 2th = 26.507° | 3.35996 | 423 | 44.2 |
| 2th = 26.730° | 3.33240 | 343 | 35.8 |
| 2th = 27.359° | 3.25726 | 326 | 34.0 |
| 2th = 27.893° | 3.19608 | 432 | 45.1 |
| 2th = 28.399° | 3.14030 | 389 | 40.6 |
| 2th = 28.918° | 3.08502 | 372 | 38.8 |
| 2th = 30.514° | 2.92722 | 311 | 32.5 |
| 2th = 31.221° | 2.86256 | 302 | 31.5 |
| 2th = 31.654° | 2.82441 | 322 | 33.6 |
| 2th = 32.085° | 2.78741 | 349 | 36.4 |
| 2th = 32.592° | 2.74517 | 308 | 32.2 |
| 2th = 33.490° | 2.67360 | 323 | 33.7 |
| 2th = 34.033° | 2.63217 | 246 | 25.7 |
| 2th = 34.608° | 2.58975 | 249 | 26.0 |
| 2th = 34.973° | 2.56357 | 314 | 32.8 |
| 2th = 35.533° | 2.52440 | 269 | 28.1 |
| 2th = 36.332° | 2.47069 | 261 | 27.2 |
| 2th = 36.772° | 2.44214 | 278 | 29.0 |
| 2th = 37.328° | 2.40703 | 225 | 23.5 |
| 2th = 38.414° | 2.34144 | 277 | 28.9 |

*Values ± 0.1°

The co-crystal thus obtained has a lower melting point, higher solubility and better workability in an aqueous medium than IPBC. In particular, its aqueous solubility is approx. 40% greater than that of IPBC.

Example 4

Co-Crystal Containing 3-iodopropynyl butylcarbamate and calcium chloride in a 4:1 Molar Ratio (Co-Crystal 4)

This example demonstrates the ability of IPBC to co-crystallise with a halide deriving from an inorganic salt such as calcium chloride.

The co-crystal was formed by mechano-chemical synthesis in a ball mill, using a stoichiometric ratio of 1:4 between calcium chloride and IPBC.

The composition of the co-crystal was detected by analysing the DSC trace, where the presence of peaks of the starting products was not observed.

The co-crystal is a solid crystalline product with a melting point of 83-86° C.

Figure 13:
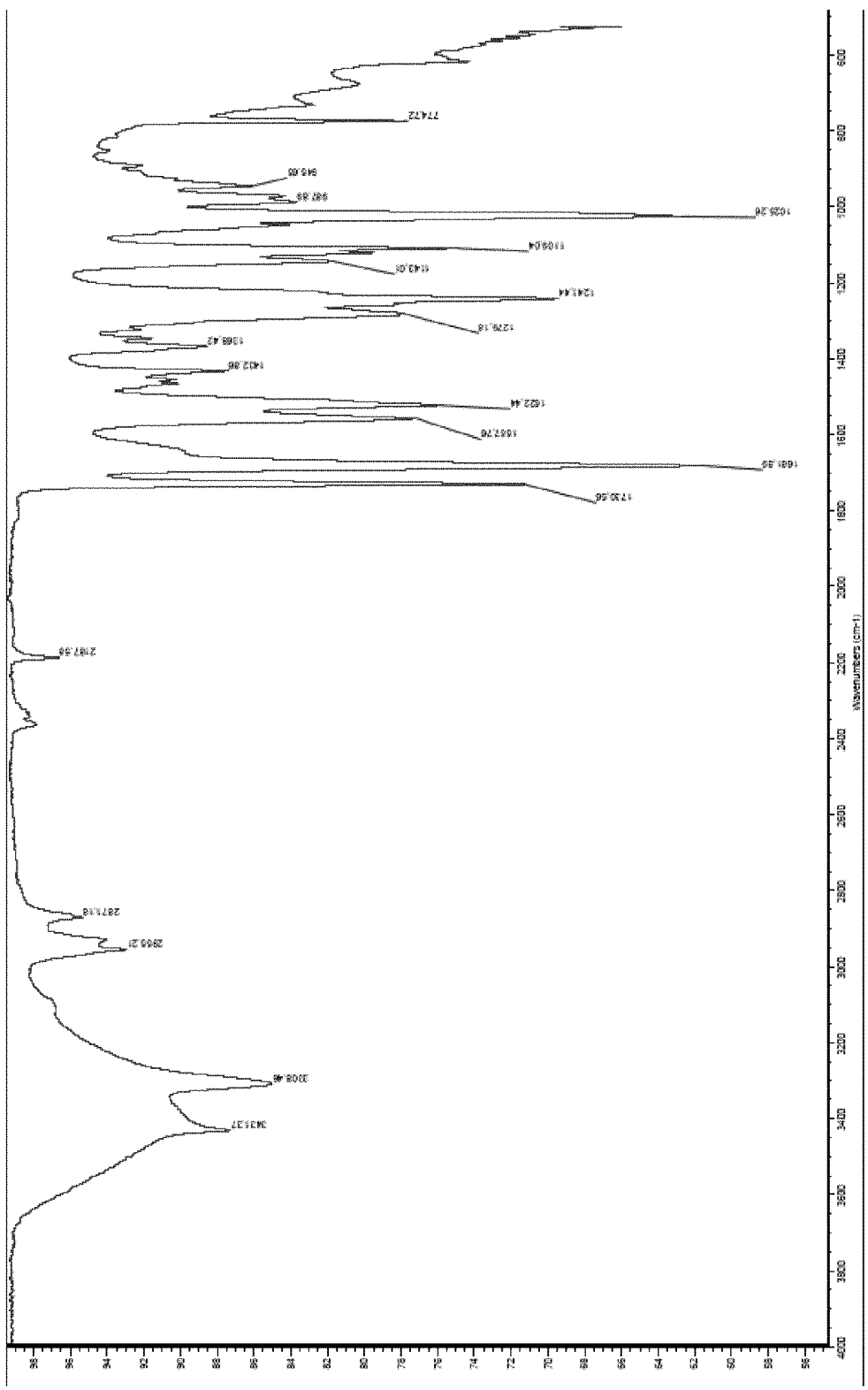
FIG. 13: API IR spectrum of the co-crystal of example 4.

The IR spectrum of the co-crystal and its characteristic bands are reported in FIG. 13.

Figure 14:
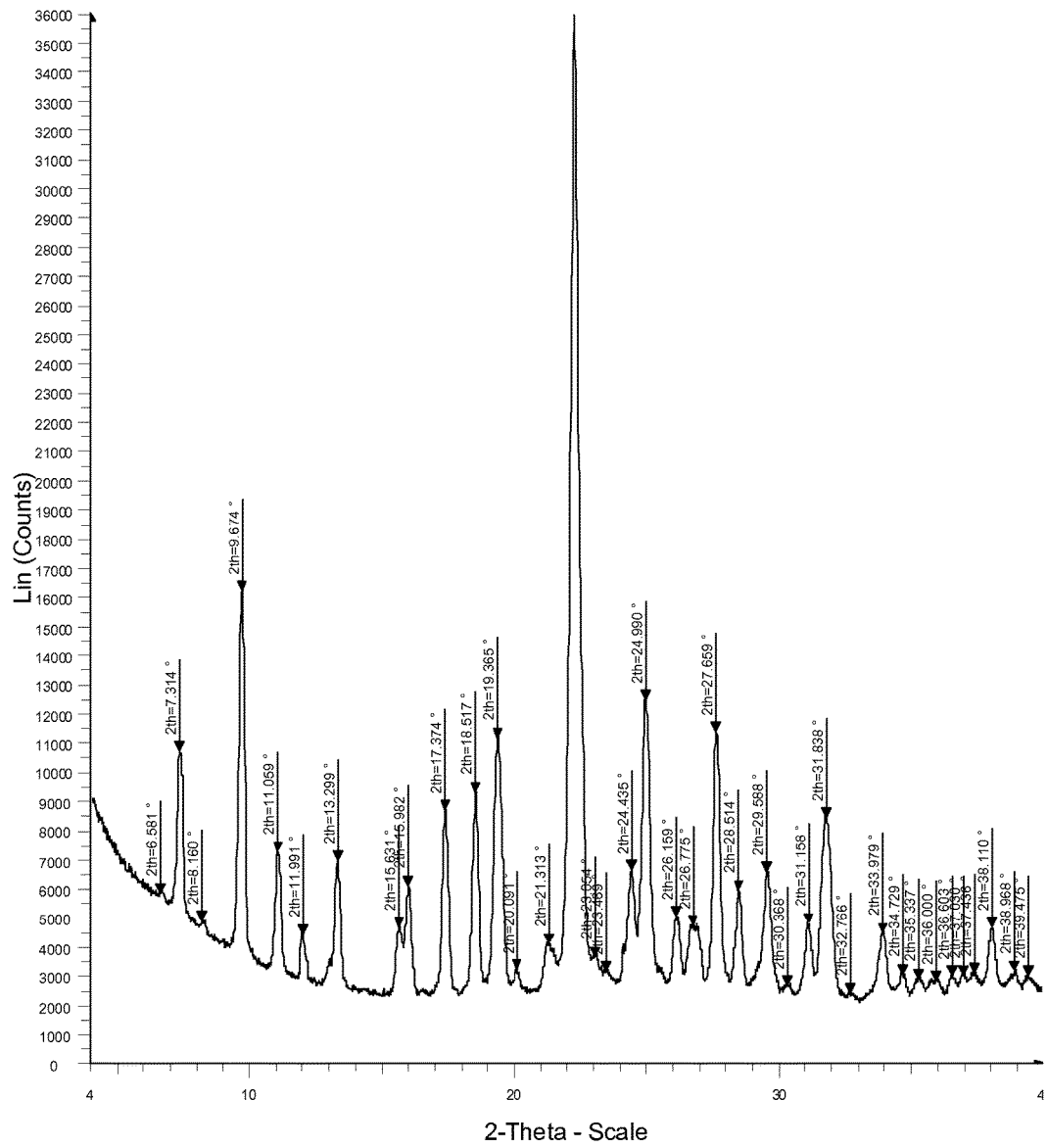
FIG. 14: XRPD tracing of the co-crystal of example 4.

FIG. 14 shows the X-ray powder diffraction (XRPD) of the co-crystal, the main peaks of which, in the 5-40° 2θ value range, are shown in Table 4.

Figure 15:
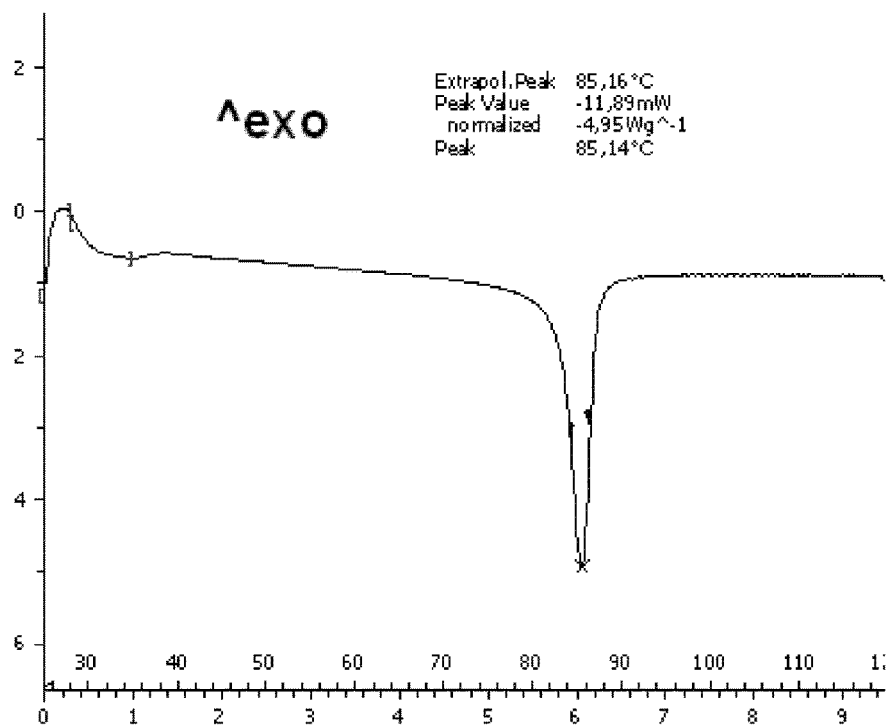
FIG. 15: DSC tracing of the co-crystal of example 4.

The DSC thermogram of co-crystal 4 is reported in FIG. 15.

TABLE 4

| Angle(2θ) | d (Å) | Intensity | % |
|---|---|---|---|
| 2th = 6.581° | 13.41984 | 5844 | 16.2 |
| 2th = 7.314° | 12.07749 | 10715 | 29.7 |
| 2th = 8.160° | 10.82602 | 4892 | 13.6 |
| 2th = 9.674° | 9.13549 | 16217 | 45.0 |
| 2th = 11.059° | 7.99382 | 7263 | 20.1 |
| 2th = 11.991° | 7.37478 | 4418 | 12.3 |
| 2th = 13.299° | 6.65245 | 6966 | 19.3 |
| 2th = 15.631° | 5.66483 | 4674 | 13.0 |
| 2th = 15.982° | 5.54118 | 6113 | 17.0 |
| 2th = 17.374° | 5.10003 | 8718 | 24.2 |
| 2th = 18.517° | 4.78765 | 9325 | 25.9 |
| 2th = 19.365° | 4.57995 | 11180 | 31.0 |
| 2th = 20.091° | 4.41616 | 3184 | 8.8 |
| 2th = 21.313° | 4.16552 | 4102 | 11.4 |
| 2th = 22.282° | 3.98664 | 36057 | 100.0 |
| 2th = 23.054° | 3.85484 | 3660 | 10.2 |
| 2th = 23.469° | 3.78751 | 3136 | 8.7 |
| 2th = 24.435° | 3.63994 | 6628 | 18.4 |
| 2th = 24.990° | 3.56041 | 12456 | 34.5 |
| 2th = 26.159° | 3.40384 | 5054 | 14.0 |
| 2th = 26.775° | 3.32689 | 4703 | 13.0 |
| 2th = 27.659° | 3.22252 | 11372 | 31.5 |
| 2th = 28.514° | 3.12789 | 5945 | 16.5 |
| 2th = 29.588° | 3.01671 | 6588 | 18.3 |
| 2th = 30.368° | 2.94095 | 2644 | 7.3 |
| 2th = 31.158° | 2.86817 | 4800 | 13.3 |
| 2th = 31.838° | 2.80850 | 8422 | 23.4 |
| 2th = 32.766° | 2.73101 | 2388 | 6.6 |

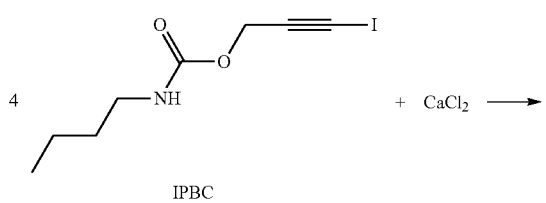

IPBC + CaCl$_2$ →

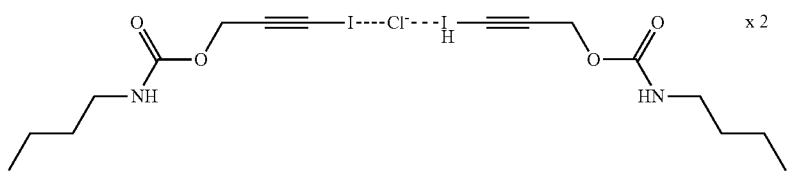

x 2

TABLE 4-continued

| Angle(2θ) | d (Å) | Intensity | % |
|---|---|---|---|
| 2th = 33.979° | 2.63621 | 4478 | 12.4 |
| 2th = 34.729° | 2.58102 | 3049 | 8.5 |
| 2th = 35.337° | 2.53800 | 2887 | 8.0 |
| 2th = 36.000° | 2.49271 | 2816 | 7.8 |
| 2th = 36.603° | 2.45308 | 2980 | 8.3 |
| 2th = 37.030° | 2.42574 | 3009 | 8.3 |
| 2th = 37.436° | 2.40037 | 3085 | 8.6 |
| 2th = 38.110° | 2.35946 | 4670 | 13.0 |
| 2th = 38.968° | 2.30947 | 3168 | 8.8 |
| 2th = 39.475° | 2.28092 | 2995 | 8.3 |

* Values ± 0.05°

The co-crystal thus obtained has a higher melting point, higher solubility and better workability in an aqueous medium than IPBC. In particular, its aqueous solubility is approx. 50% greater than that of IPBC.

Example 5

Co-Crystal Containing 3-iodopropynyl butylcarbamate and N,N'-bis(4-pyridylcarbonyl)-1,6-hexanediamine in a 2:1 Molar Ratio (Co-Crystal 5)

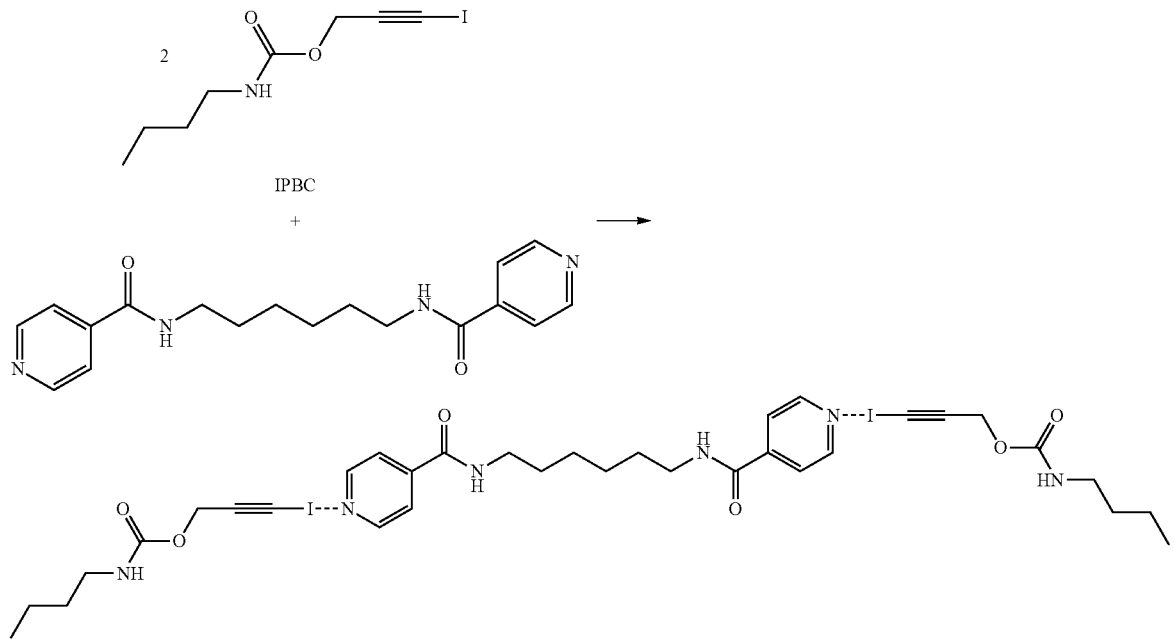

In this example, IPBC was co-crystallised with N,N'-bis(4-pyridylcarbonyl)-1,6-hexanediamine by slow evaporation from alcohol solutions and by mechano-chemical synthesis in a ball mill, using a ratio of 1:2 between the co-crystallisation agent and IPBC.

Figure 16:
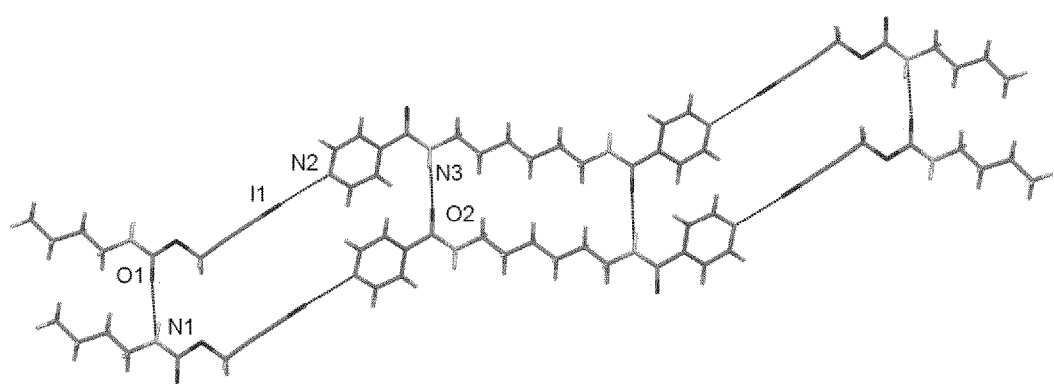
FIG. 16: Graphical representation of the co-crystal of example 5.

In the co-crystal obtained there is a ratio of 1:2 between the co-crystallisation agent and IPBC, as shown in the graphical representation in FIG. 16.

The co-crystal is a solid crystalline product with a melting point of 132° C. The dimensions and angles of the crystallographic unit cell are [a=29.4501(18) b=5.1100(3) c=27.9417(17)] and [α=90.00 β=118.566(3) γ=90.00] respectively.

Figure 17:
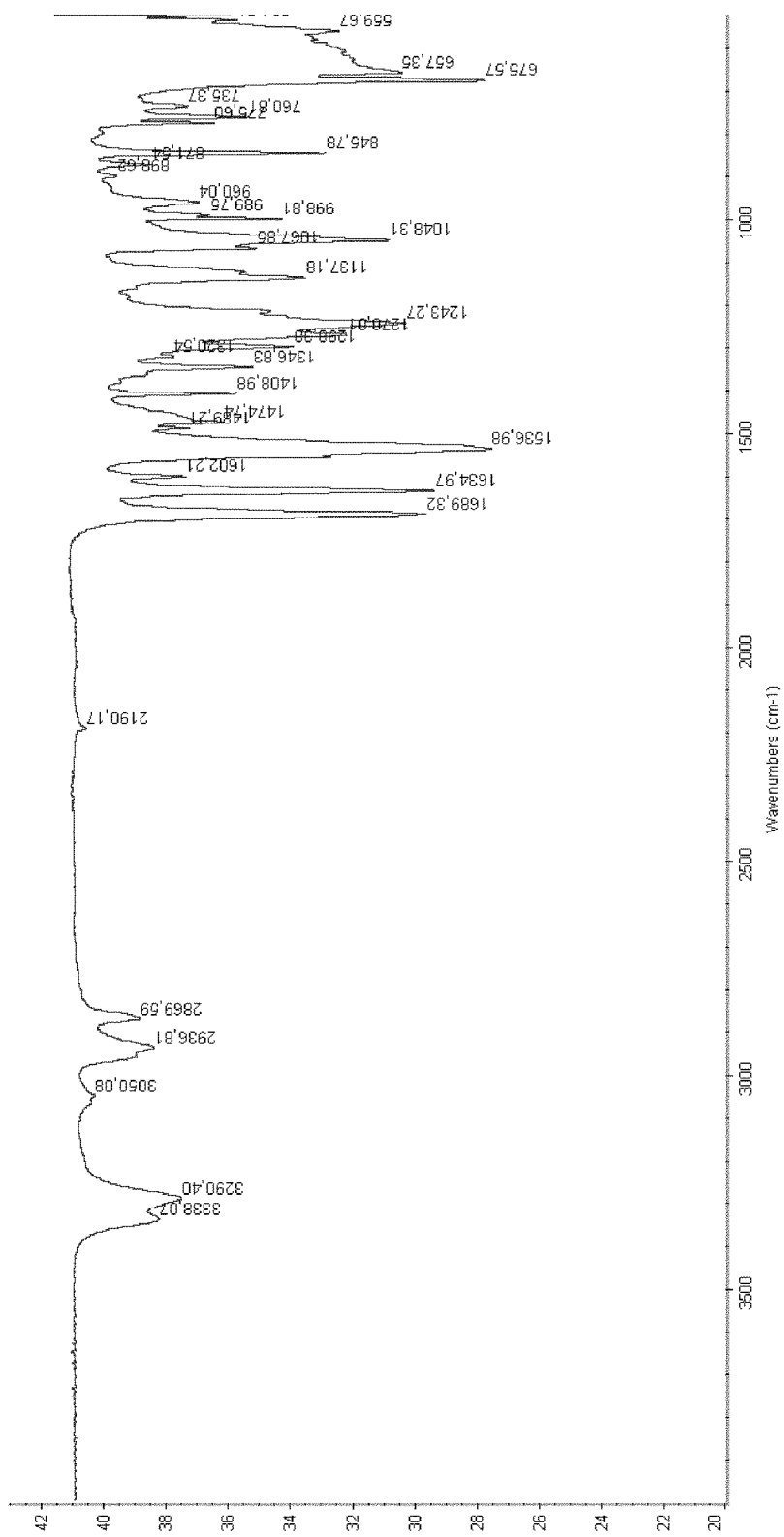
FIG. 17: API IR spectrum of the co-crystal of example 5.

The IR spectrum of the co-crystal and its characteristic bands are reported in FIG. 17.

Figure 18:
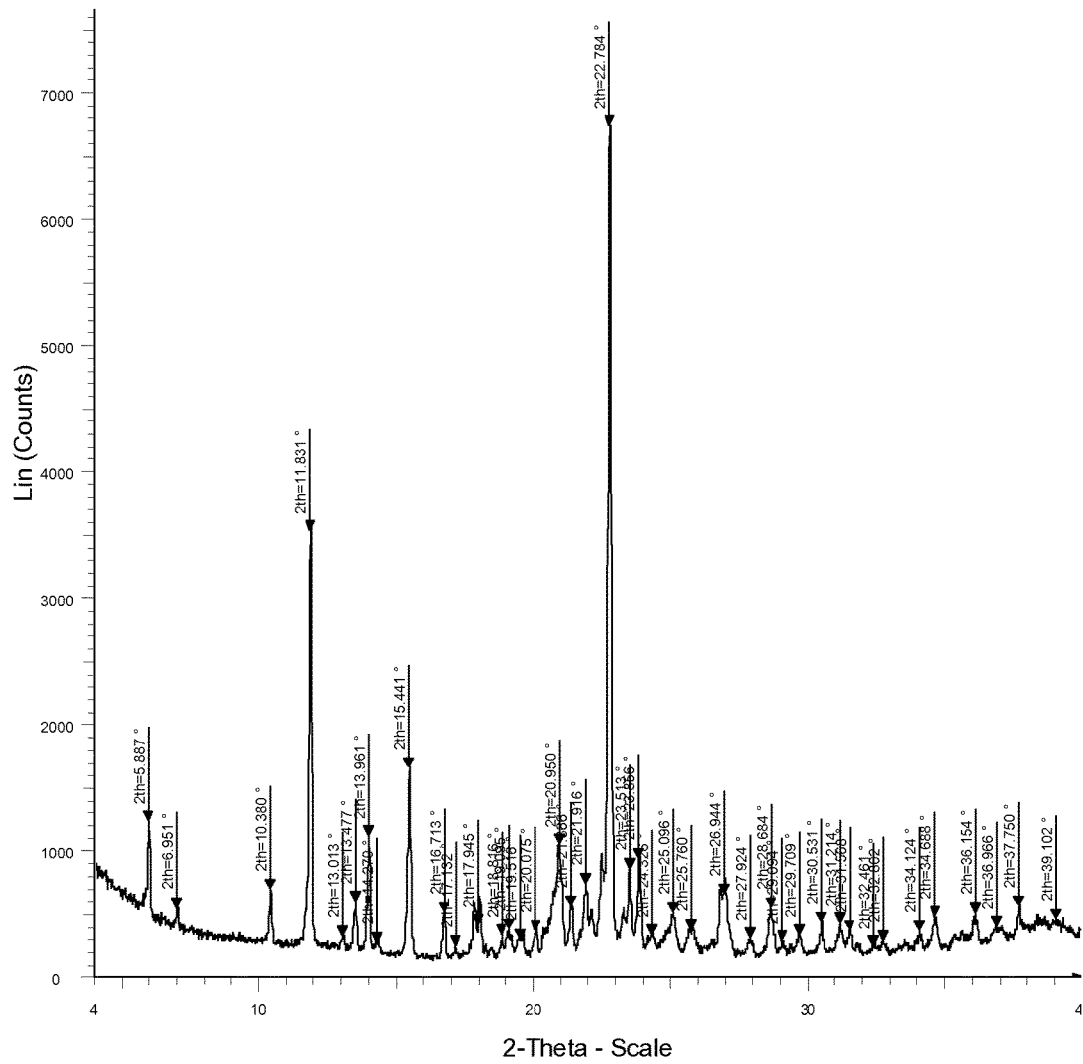
FIG. 18: XRPD tracing of the co-crystal of example 5.

FIG. 18 shows the X-ray powder diffraction (XRPD) of the co-crystal, the main peaks of which, in the 5-40° 2θ value range, are shown in Table 5.

Figure 19:
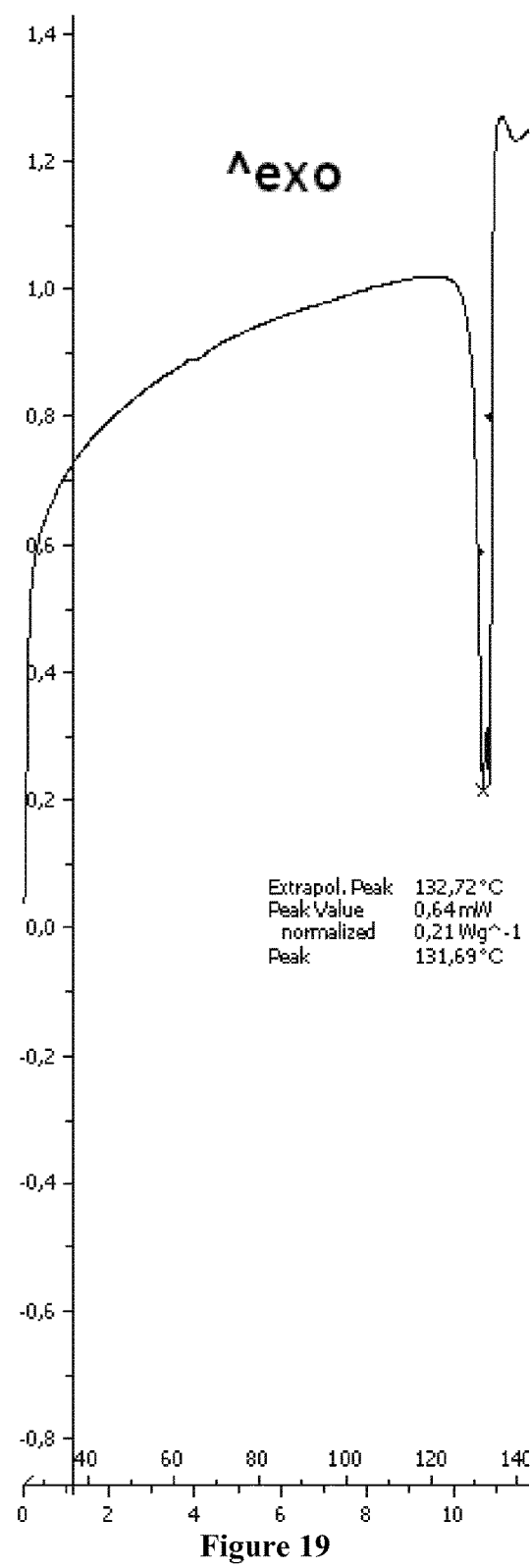
FIG. 19: DSC tracing of the co-crystal of example 5.

The DSC thermogram of co-crystal 5 is reported in FIG. 19.

TABLE 5

| Angle(2θ) | d (Å) | Intensity | % |
|---|---|---|---|
| 2th = 5.887° | 14.99966 | 1231 | 18.2 |
| 2th = 6.951° | 12.70619 | 545 | 8.1 |
| 2th = 10.380° | 8.51551 | 690 | 10.2 |
| 2th = 11.831° | 7.47444 | 3530 | 52.3 |
| 2th = 13.013° | 6.79759 | 324 | 4.8 |
| 2th = 13.477° | 6.56468 | 591 | 8.8 |
| 2th = 13.961° | 6.33814 | 1111 | 16.5 |
| 2th = 14.270° | 6.20161 | 272 | 4.0 |
| 2th = 15.441° | 5.73399 | 1653 | 24.5 |
| 2th = 16.713° | 5.30018 | 510 | 7.6 |
| 2th = 17.132° | 5.17156 | 244 | 3.6 |
| 2th = 17.945° | 4.93909 | 411 | 6.1 |
| 2th = 18.816° | 4.71240 | 331 | 4.9 |
| 2th = 19.095° | 4.64417 | 378 | 5.6 |
| 2th = 19.516° | 4.54479 | 300 | 4.4 |
| 2th = 20.075° | 4.41964 | 366 | 5.4 |

TABLE 5-continued

| Angle(2θ) | d (Å) | Intensity | % |
|---|---|---|---|
| 2th = 20.950° | 4.23697 | 1050 | 15.6 |
| 2th = 21.366° | 4.15541 | 563 | 8.3 |
| 2th = 21.916° | 4.05229 | 740 | 11.0 |
| 2th = 22.784° | 3.89988 | 6751 | 100.0 |
| 2th = 23.513° | 3.78060 | 855 | 12.7 |
| 2th = 23.856° | 3.72703 | 939 | 13.9 |
| 2th = 24.326° | 3.65609 | 332 | 4.9 |
| 2th = 25.096° | 3.54550 | 509 | 7.5 |
| 2th = 25.760° | 3.45568 | 376 | 5.6 |
| 2th = 26.944° | 3.30641 | 653 | 9.7 |
| 2th = 27.924° | 3.19254 | 305 | 4.5 |
| 2th = 28.684° | 3.10973 | 548 | 8.1 |
| 2th = 29.094° | 3.06678 | 276 | 4.1 |
| 2th = 29.709° | 3.00471 | 330 | 4.9 |

TABLE 5-continued

| Angle(2θ) | d (Å) | Intensity | % |
|---|---|---|---|
| 2th = 30.531° | 2.92568 | 430 | 6.4 |
| 2th = 31.214° | 2.86315 | 419 | 6.2 |
| 2th = 31.568° | 2.83188 | 367 | 5.4 |
| 2th = 32.461° | 2.75600 | 241 | 3.6 |

TABLE 5-continued

| Angle(2θ) | d (Å) | Intensity | % |
|---|---|---|---|
| 2th = 32.802° | 2.72810 | 284 | 4.2 |
| 2th = 34.124° | 2.62537 | 365 | 5.4 |
| 2th = 34.688° | 2.58393 | 478 | 7.1 |
| 2th = 36.154° | 2.48246 | 505 | 7.5 |
| 2th = 36.966° | 2.42976 | 398 | 5.9 |
| 2th = 37.750° | 2.38110 | 561 | 8.3 |
| 2th = 39.102° | 2.30185 | 457 | 6.8 |

* Values ± 0.05°

The co-crystal thus obtained has a higher melting point, higher thermal stability, better workability and higher degree of crystallinity than IPBC. It is easily manageable in the operations required to form tablets, such as compression.

Example 6

Co-Crystal Containing 3-iodopropynyl butylcarbamate and pyridine in a 1:1 Molar Ratio (Co-Crystal 6)

In this example, IPBC was co-crystallised with pyridine.
The co-crystal was prepared dissolving in the 1:1 molar ratio IPBC in pyridine.

The cocrystal is liquid at room temperature, but the formation of a halogen bonded system between IPBC and pyridine can be confirmed looking at the chemical shift variation of $^{13}$C-NMR for the carbon bound to iodine.

Figure 20:
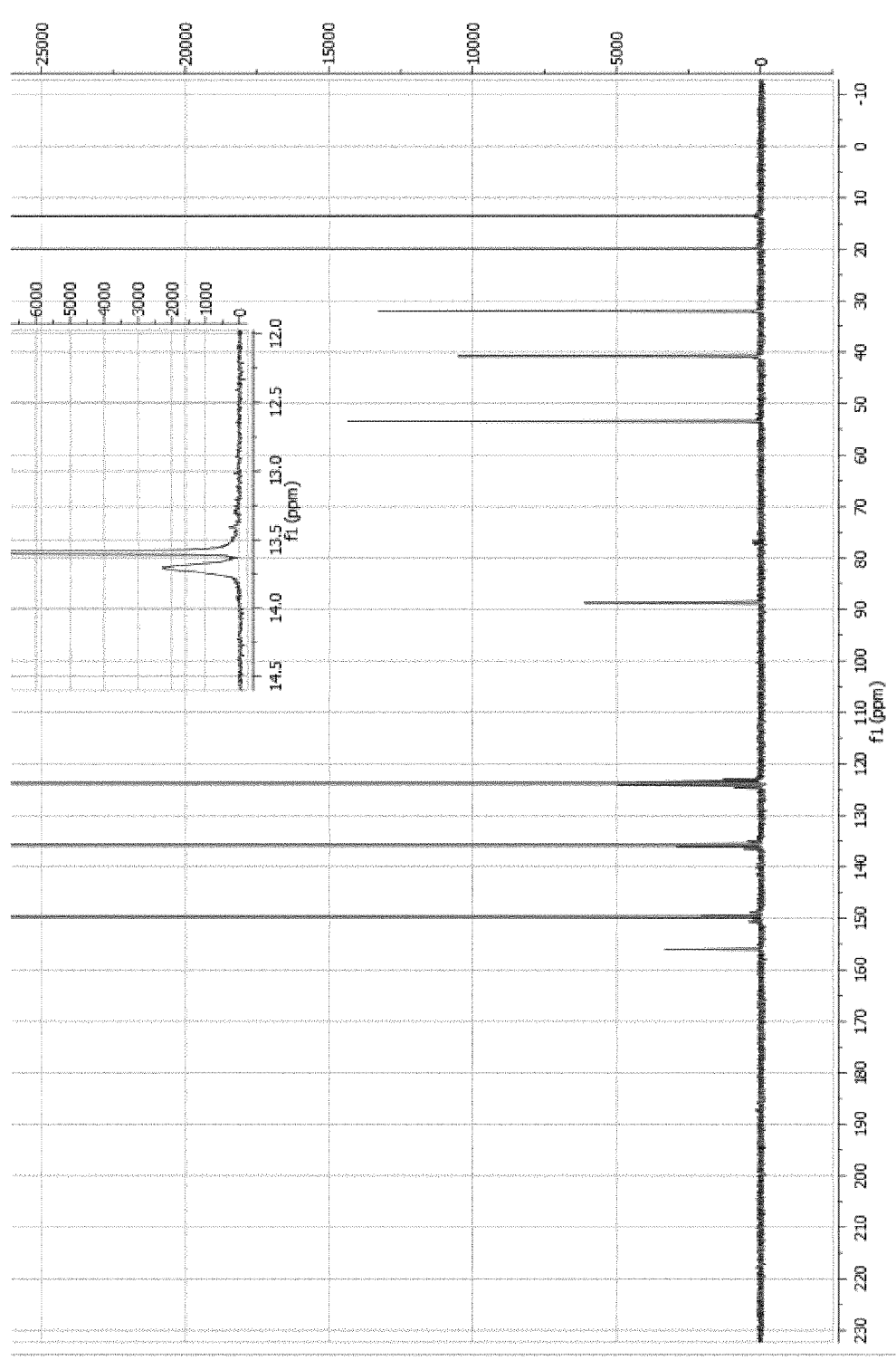
FIG. 20: $^{13}$C-NMR of the co-crystal of example 6.

Previous studies have demonstrated that the $^{13}$C signals of the iodinated carbons of iodoethynyl moieties undergo major low-field shifts on changing the solvent from chloroform to dimethylsulphoxide as a consequence of the XB occurring with the oxygen atoms of the solvent. [ref. Rege, P. D.; Malkina, O. L.; Goroff, N. S. *J. Am. Chem. Soc.* 2002, 124, 370-371. Gao, K.; Goroff, N. S. *J. Am. Chem. Soc.* 2000, 122, 9320-9321.]. The ≡C—I signals of deuterochloroform solutions of pure IPBC is at 3.68 ppm, in the cocrystal with pyridine the ≡C—I chemical shift varies from 4.00 ppm up to 14 ppm depending of the concentration of pyridine used, as shown in FIG. 20.

Example 7

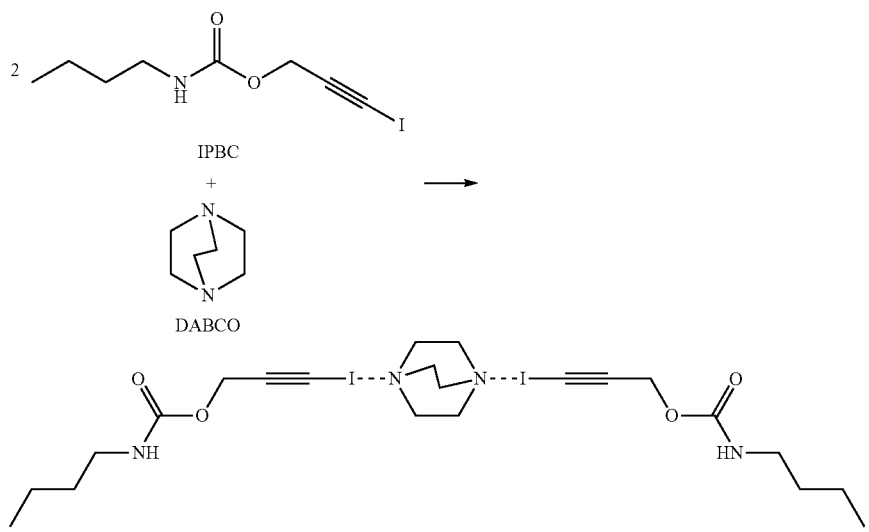

Co-Crystal Containing 3-iodopropynyl butylcarbamate and 1,4-diazabicyclo[2.2.2]octane (DABCO) in a 2:1 Molar Ratio (Co-Crystal 7)

In this example, IPBC was co-crystallised with the bicyclic tertiary amine 1,4-diazabicyclo[2.2.2]octane (DABCO), to give a co-crystal IPBC:DABCO with molar ratio 2:1.

IPBC was co-crystallised with DABCO by slow evaporation from alcohol/haloalkane solutions, using a ratio of 1:2 between the co-crystallisation agent and IPBC.

Melting point: 35-38° C.

Figure 21:
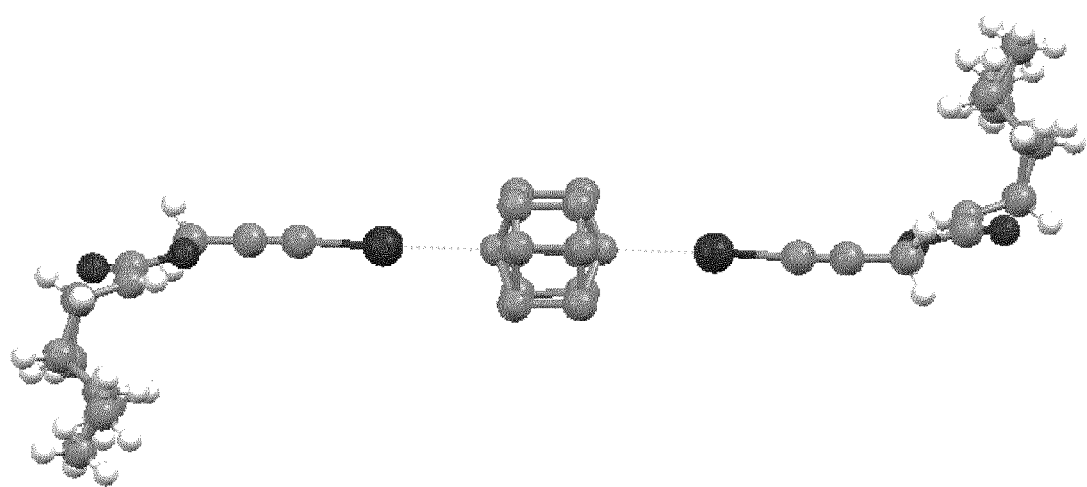
FIG. 21: Ball and stick representation from single crystal analysis of the co-crystal of example 7. DABCO hydrogen atoms are omitted for clarity.

The structure of the IPBC.DABCO co-crystal from single crystal crystallographic analysis is shown in FIG. 21, wherein DABCO hydrogen atoms are omitted for clarity.

Crystallographic data: orthorhombic, Pccn, a: 9.8955(7); b: 31.623(2); c: 8.9335(6) and V=2795.55 Å$^3$.

Example 8

Co-Crystal Containing 3-iodopropynyl butylcarbamate and tetrabutylammonium chloride (TBACl) in a 2:1 Molar Ratio (Co-Crystal 8)

In this example, IPBC was co-crystallised with tetrabutylammonium chloride (TBACl) to give a IPBC:TBACl co-crystal with molar ratio 2:1.

The co-crystal was formed by heating the two components up to 50° C. using a stoichiometric ratio of 1:2 between tetrabutyl ammonium chloride and IPBC.

The co-crystal is liquid at room temperature.

Melting point −15° C.

Figure 22:
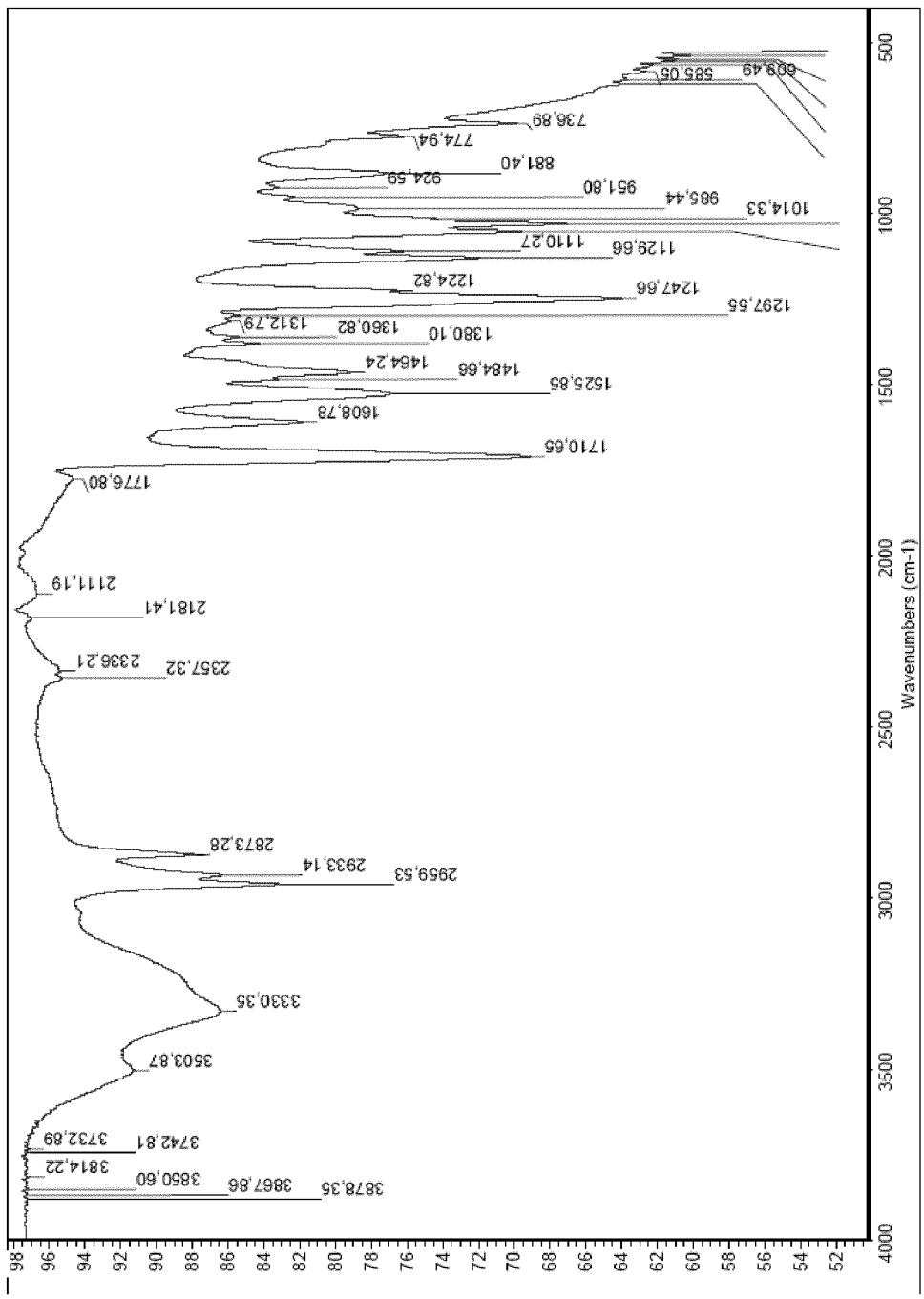
FIG. 22: IR spectrum of the co-crystal of example 8.

The formation of a halogen bonded co-crystal between IPBC and TBACl can be confirmed looking at the IR wave number variation for C≡C group. The triple bond stretching band is at 2198 cm$^{-1}$ in the pure IPBC while it is red-shifted at 2181 cm$^{-1}$ for the (IPBC)$_2$:TBACl cocrystal, as shown in FIG. 22.

Example 9

Co-Crystal Containing 3-iodopynyl butylcarbamate and zinc chloride in a 4:1 Molar Ratio (Co-Crystal 9)

This example demonstrates the ability of IPBC to co-crystallise with a halide deriving from a transition metal, such as zinc chloride, to give a IPBC:ZnCl$_2$ co-crystal with molar ratio 4:1

The co-crystal was prepared using the same procedure employed for example 4.

Figure 23:
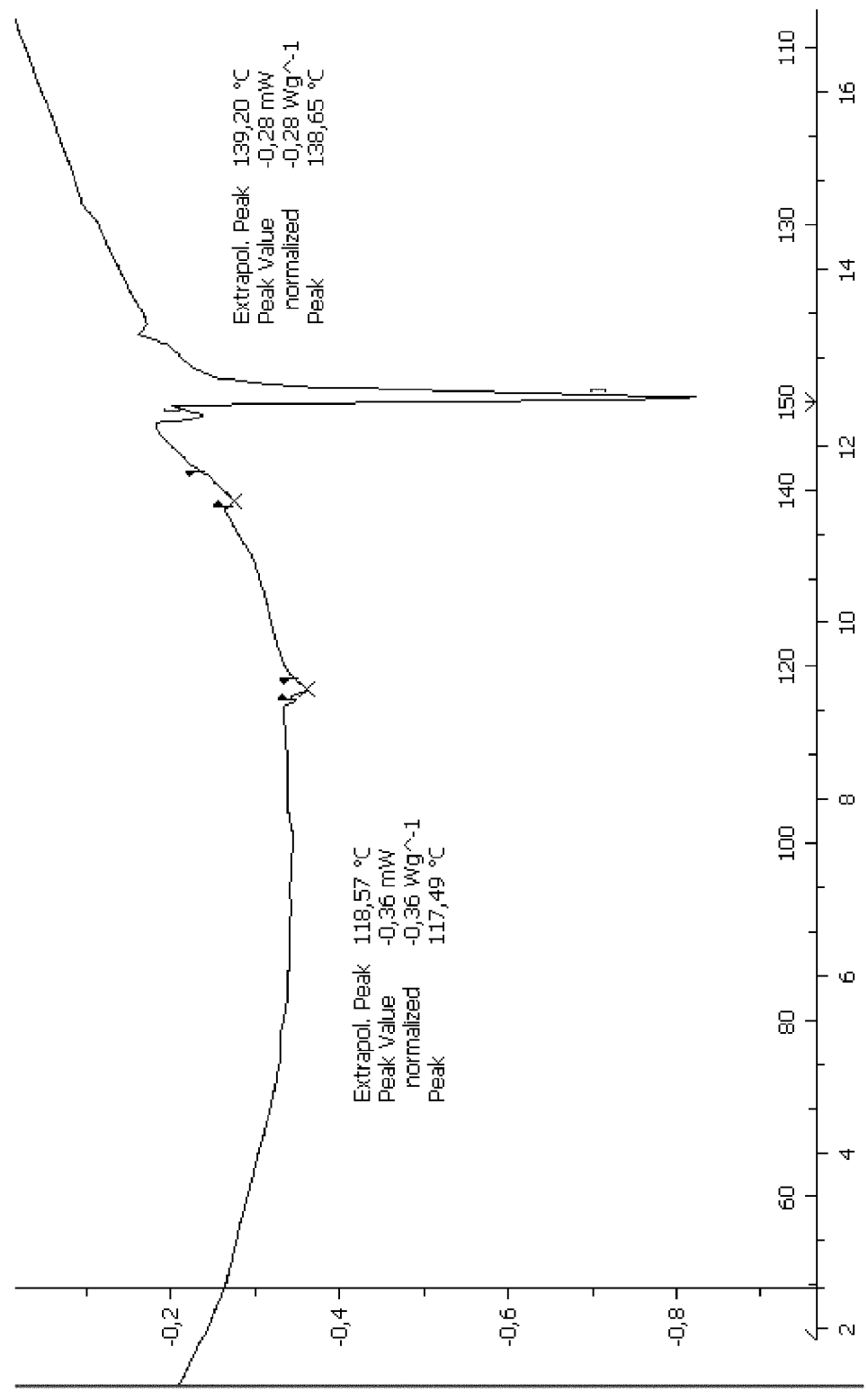
FIG. 23: DSC plot of the co-crystal of example 9.

The formation of a halogen bonded cocrystal between IPBC and ZnCl$_2$ can be confirmed looking at the DSC plot (FIG. 23) showing two peaks at 118° C. and 139° C. (mixture of polymorphs) and the absence of the IPBC melting peak.

Example 10

Figure 24:
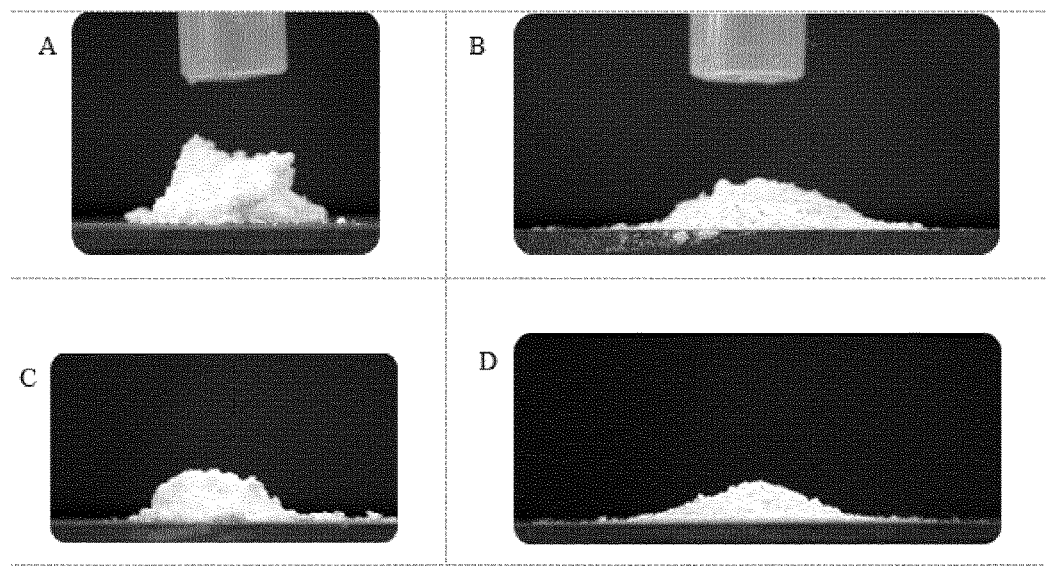
FIG. 24: Pictures of cones of pure IPBC (A, C) and co-crystal (IPBC)$_4$:CaCl$_2$ (B, D) powders, taken after flowing the powders through the funnel.

Evaluation of Flowing Characteristics of Powders Containing the Halogen Bonded (IPBC)$_4$:CaCl$_2$ Complex or Pure IPBC In this example the angle of response of powders containing the halogen bonded (IPBC)$_4$:CaCl$_2$ complex of example 4 was compared to that of powders containing pure IPBC (FIG. 24). The angle of response estimates the flow characteristics of the powders, The use of pure IPBC in industrial products faces significant manufacturing drawbacks. IPBC is difficult to handle because it tends to be clumpy and sticky, this implies that it cannot be fed easily from the blending equipment and the automatic feeding device.

FIG. 24 shows that the cohesive properties of powder for co-crystal (IPBC)$_4$:CaCl$_2$ are drastically different compared to the pure IPBC. Co-crystal (IPBC)$_4$:CaCl$_2$ has values of angle of repose between 13° and 20° which indicates that it has excellent free-flow powder characteristic. On the contrary for the pure IPBC it is impossible to evaluate any angle of repose since the cohesive forces in the powder are too strong and its powder does not form an appropriate cone shape but tends to aggregate in irregular pillared shape. The cylindrical shape of IPBC cones indicates clearly the high cohesion of the powders, while the flat cone shape of co-crystal (IPBC)$_4$:CaCl$_2$ indicates improved flow powder properties.

The invention claimed is:

1. A co-crystal of the compound 3-iodopropynyl butyl carbamate with a co-crystallisation agent, wherein said co-crystal is selected from the group of: co-crystal containing 3-iodopropynyl butyl carbamate and pyridine in a 1:1 molar ratio;
   co-crystal containing 3-iodopropynyl butyl carbamate and 4-[2-(4-pyridinyl)ethyl]pyridine in a 2:1 molar ratio;
   co-crystal containing 3-iodopropynyl butyl carbamate and 4,4'-bipyridine in a 2:1 molar ratio;
   co-crystal containing 3-iodopropynyl butyl carbamate and 1,4-diazabicyclo[2.2.2]octane in a 2:1 molar ratio;
   co-crystal containing 3-iodopropynyl butyl carbamate and tetrabutylammonium iodide in a 3:1 molar ratio;
   co-crystal containing 3-iodopropynyl butyl carbamate and tetrabutylammonium chloride in a 2:1 molar ratio;
   co-crystal containing 3-iodopropynyl butyl carbamate and calcium chloride in a 4:1 molar ratio;
   co-crystal containing 3-iodopropynyl butyl carbamate and zinc chloride in a 4:1 molar ratio;
   and co-crystal containing 3-iodopropynyl butyl carbamate and N,N'-bis(4-pyridylcarbonyl)-1,6-hexanediamine in a 2:1 molar ratio.

2. A co-crystal according to claim 1, wherein the co-crystallisation agent is tetrabutylammonium iodide or tetrabutylammonium chloride.

3. A co-crystal according to claim 1, wherein the co-crystallisation agent is calcium chloride or zinc chloride.

4. A composition containing a co-crystal of claim 1, a solvent or diluent and optionally additives and/or a biocidal agent.

5. Industrial products containing a co-crystal as defined in claim 1.

6. A method of protecting and preserving wood, personal care products or cosmetic formulations with the composition according to claim 4, said method comprising adding said composition to industrial formulations selected from the group consisting essentially of paints, coatings and metal-working fluids to provide a biocide, preservative, antibacterial, fungicide or algaecide protection to said paints, coatings and metal working fluids for protecting and preserving said wood, body care products or cosmetic formulations.

7. Process for the preparation of a co-crystal as defined in claim 1, comprising the steps of:
   a) contacting 3-iodopropynyl butyl carbamate with a co-crystallization agent able to form at least one halogen bond with said 3-iodopropynyl butyl carbamate, under crystallisation conditions able to form a solid phase wherein 3-iodopropynyl butyl carbamate and said co-crystallisation agent are bound to each other through at least one halogen bond;
   b) optional isolation of the co-crystals formed in step a).

* * * * *